US010105485B2

(12) United States Patent
Piferi et al.

(10) Patent No.: US 10,105,485 B2
(45) Date of Patent: Oct. 23, 2018

(54) MRI SURGICAL SYSTEMS INCLUDING MRI-COMPATIBLE SURGICAL CANNULAE FOR TRANSFERRING A SUBSTANCE TO AND/OR FROM A PATIENT

(75) Inventors: Peter Piferi, Orange, CA (US); Kimble Jenkins, Memphis, TN (US)

(73) Assignee: MRI Interventions, Inc., Irvine, CA (US)

( * ) Notice: Subject to any disclaimer, the term of this patent is extended or adjusted under 35 U.S.C. 154(b) by 839 days.

(21) Appl. No.: 13/640,251

(22) PCT Filed: Apr. 8, 2011

(86) PCT No.: PCT/US2011/031678
§ 371 (c)(1),
(2), (4) Date: Oct. 9, 2012

(87) PCT Pub. No.: WO2011/130107
PCT Pub. Date: Oct. 20, 2011

(65) Prior Publication Data
US 2013/0030408 A1    Jan. 31, 2013

Related U.S. Application Data

(60) Provisional application No. 61/324,990, filed on Apr. 16, 2010.

(51) Int. Cl.
*A61M 5/158* (2006.01)
*A61B 17/00* (2006.01)
(Continued)

(52) U.S. Cl.
CPC ............ *A61M 5/1582* (2013.01); *A61B 5/055* (2013.01); *A61B 5/4076* (2013.01); *A61B 90/11* (2016.02);
(Continued)

(58) Field of Classification Search
CPC ..... A61B 5/14865; A61B 5/415; A61B 5/418; A61B 5/684
See application file for complete search history.

(56) References Cited

U.S. PATENT DOCUMENTS 3,352,306 A    11/1967   Hirsch
3,540,447 A    11/1970   Howe
(Continued)

FOREIGN PATENT DOCUMENTS

EP    1 334 740 A1    8/2003
EP    1 491 154 A1    12/2004
(Continued)

OTHER PUBLICATIONS

Chen M.Y. et al., "Surface properties, more than size, limiting convective distribution of virus-sized particles and viruses in the central nervous system", *J Neurosurg*, 103:311-319, 2005.
(Continued)

*Primary Examiner* — Bhisma Mehta
*Assistant Examiner* — Matthew A Engel
(74) *Attorney, Agent, or Firm* — Myers Bigel, P.A.

(57) ABSTRACT

A cannula for transferring a substance to and/or from a patient includes a tubular support sleeve and a transfer tube. The support sleeve includes a rigid tubular member defining a lumen extending from a proximal end to a distal end of the tubular member. The transfer tube is positioned in the lumen and extends beyond each of the proximal end and the distal end of the tubular member. The tubular member includes a rigid, MRI-compatible material.

19 Claims, 21 Drawing Sheets

(51) Int. Cl.
*A61B 5/055* (2006.01)
*A61M 25/00* (2006.01)
*A61M 25/01* (2006.01)
*A61B 5/00* (2006.01)
*A61B 90/11* (2016.01)
*A61B 17/34* (2006.01)
*A61B 34/00* (2016.01)
*A61B 90/00* (2016.01)

(52) U.S. Cl.
CPC ...... *A61M 25/007* (2013.01); *A61M 25/0105* (2013.01); *A61M 25/0108* (2013.01); *A61B 34/25* (2016.02); *A61B 2017/0088* (2013.01); *A61B 2017/00849* (2013.01); *A61B 2017/00911* (2013.01); *A61B 2017/3407* (2013.01); *A61B 2017/3409* (2013.01); *A61B 2090/034* (2016.02); *A61B 2090/374* (2016.02); *A61B 2090/3954* (2016.02); *A61M 2025/0004* (2013.01); *A61M 2025/0166* (2013.01); *A61M 2205/0211* (2013.01)

(56) References Cited

U.S. PATENT DOCUMENTS

| | | | |
|---|---|---|---|
| 3,824,157 A * | 7/1974 | Macur | A61B 5/14539 205/782.5 |
| 3,856,009 A * | 12/1974 | Winnie | A61M 25/0606 604/170.03 |
| 4,149,535 A | 4/1979 | Volder | |
| 4,239,042 A * | 12/1980 | Asai | A61M 25/0111 128/207.29 |
| 4,265,928 A * | 5/1981 | Braun | A61L 33/064 427/2.25 |
| 4,327,722 A * | 5/1982 | Groshong | A61M 5/158 604/510 |
| 4,449,532 A | 5/1984 | Storz | |
| 4,531,943 A * | 7/1985 | Van Tassel | A61M 25/0069 600/435 |
| 4,543,091 A | 9/1985 | Froning et al. | |
| 4,543,092 A | 9/1985 | Mehler et al. | |
| 4,597,421 A | 7/1986 | Wells | |
| 4,623,789 A | 11/1986 | Ikeda et al. | |
| 4,629,450 A | 12/1986 | Suzuki et al. | |
| 4,705,511 A | 11/1987 | Kocak | |
| 4,738,658 A | 4/1988 | Magro et al. | |
| 4,739,768 A | 4/1988 | Engelson | |
| 4,781,691 A | 11/1988 | Gross | |
| 4,820,349 A * | 4/1989 | Saab | A61M 25/1029 604/913 |
| 4,846,799 A * | 7/1989 | Tanaka | A61M 5/32 604/158 |
| 4,897,077 A * | 1/1990 | Cicciu | A61M 39/0606 600/18 |
| 4,955,863 A * | 9/1990 | Walker | A61M 25/0014 604/165.02 |
| 4,978,334 A | 12/1990 | Toye et al. | |
| 4,995,866 A | 2/1991 | Amplatz et al. | |
| 5,069,673 A | 12/1991 | Shwab | |
| 5,380,292 A | 1/1995 | Wilson | |
| 5,562,626 A | 10/1996 | Sanpietro | |
| 5,699,801 A | 12/1997 | Atalar et al. | |
| 5,720,720 A | 2/1998 | Laske et al. | |
| 5,792,144 A * | 8/1998 | Fischell | A61F 2/958 606/108 |
| 5,833,662 A | 11/1998 | Stevens | |
| 5,851,203 A | 12/1998 | Van Muiden | |
| 5,857,999 A * | 1/1999 | Quick | A61B 17/3421 604/104 |
| 5,871,470 A | 2/1999 | McWha | |
| 5,902,282 A | 5/1999 | Balbierz | |
| 5,919,171 A | 7/1999 | Kira et al. | |
| 5,928,145 A | 7/1999 | Ocali et al. | |
| 6,020,196 A | 2/2000 | Hu et al. | |
| 6,026,316 A | 2/2000 | Kucharczyk et al. | |
| 6,030,369 A | 2/2000 | Engelson et al. | |
| 6,042,579 A | 3/2000 | Elsberry et al. | |
| 6,050,992 A | 4/2000 | Nichols | |
| 6,093,180 A | 7/2000 | Elsberry | |
| 6,167,311 A | 12/2000 | Rezai | |
| 6,186,986 B1 | 2/2001 | Berg et al. | |
| 6,263,229 B1 | 7/2001 | Atalar et al. | |
| 6,284,971 B1 | 9/2001 | Atalar et al. | |
| RE37,410 E | 10/2001 | Brem et al. | |
| 6,309,634 B1 | 10/2001 | Bankiewicz et al. | |
| 6,336,915 B1 | 1/2002 | Scarfone et al. | |
| 6,356,786 B1 | 3/2002 | Rezai et al. | |
| 6,405,079 B1 | 6/2002 | Ansarinia | |
| 6,438,423 B1 | 8/2002 | Rezai et al. | |
| 6,524,299 B1 | 2/2003 | Tran et al. | |
| 6,526,318 B1 | 2/2003 | Ansarinia | |
| 6,533,751 B2 | 3/2003 | Cragg et al. | |
| 6,539,263 B1 | 3/2003 | Schiff et al. | |
| 6,551,290 B1 | 4/2003 | Elsberry | |
| 6,585,694 B1 | 7/2003 | Smith et al. | |
| 6,606,513 B2 | 8/2003 | Lardo et al. | |
| 6,609,030 B1 | 8/2003 | Rezai et al. | |
| 6,628,980 B2 | 9/2003 | Atalar et al. | |
| 6,641,555 B1 | 11/2003 | Botich et al. | |
| 6,641,564 B1 | 11/2003 | Kraus | |
| 6,675,033 B1 | 1/2004 | Lardo et al. | |
| 6,701,176 B1 | 3/2004 | Halperin et al. | |
| 6,708,064 B2 | 3/2004 | Rezai | |
| 6,904,307 B2 | 6/2005 | Karmarkar et al. | |
| 7,037,295 B2 | 5/2006 | Tiernan et al. | |
| 7,182,944 B2 | 2/2007 | Bankiewicz | |
| 7,329,262 B2 | 2/2008 | Gill | |
| 7,341,577 B2 | 3/2008 | Gill | |
| 7,351,239 B2 | 4/2008 | Gill | |
| 7,371,225 B2 | 5/2008 | Oldfield et al. | |
| 7,780,692 B2 * | 8/2010 | Nance | A61B 17/3417 606/198 |
| 7,815,623 B2 | 10/2010 | Bankiewicz et al. | |
| 7,892,203 B2 * | 2/2011 | Lenker | A61B 17/3439 604/103.05 |
| 7,951,110 B2 * | 5/2011 | Bishop | A61B 17/7083 604/96.01 |
| 8,128,600 B2 | 3/2012 | Gill | |
| 8,175,677 B2 | 5/2012 | Sayler et al. | |
| 8,195,272 B2 | 6/2012 | Piferi et al. | |
| 8,315,689 B2 | 11/2012 | Jenkins et al. | |
| 8,340,743 B2 | 12/2012 | Jenkins et al. | |
| 8,348,892 B2 * | 1/2013 | Lenker | A61B 17/3439 604/103.05 |
| 8,374,677 B2 | 2/2013 | Piferi et al. | |
| 8,597,277 B2 * | 12/2013 | Lenker | A61B 17/3439 264/301 |
| 8,827,987 B2 | 9/2014 | Fielder et al. | |
| 8,900,214 B2 * | 12/2014 | Nance | A61B 17/3439 604/509 |
| 9,044,577 B2 * | 6/2015 | Bishop | A61B 17/7083 |
| 9,050,419 B2 * | 6/2015 | Farnan | A61M 1/3653 |
| 9,452,241 B2 | 9/2016 | Gill et al. | |
| 2002/0087152 A1 | 7/2002 | Mikus et al. | |
| 2002/0091372 A1 | 7/2002 | Cragg et al. | |
| 2002/0095081 A1 | 7/2002 | Vilsmeier | |
| 2002/0114780 A1 | 8/2002 | Bankiewicz et al. | |
| 2002/0141980 A1 | 10/2002 | Bankiewicz et al. | |
| 2002/0183763 A1 * | 12/2002 | Callol | A61F 2/856 606/108 |
| 2003/0028095 A1 | 2/2003 | Tulley et al. | |
| 2003/0050557 A1 | 3/2003 | Susil et al. | |
| 2003/0073934 A1 | 4/2003 | Putz | |
| 2003/0216714 A1 | 11/2003 | Gill | |
| 2004/0046557 A1 | 3/2004 | Karmarkar et al. | |
| 2004/0092879 A1 | 5/2004 | Kraus et al. | |
| 2004/0199129 A1 * | 10/2004 | DiMatteo | A61M 39/0208 604/288.02 |
| 2004/0209810 A1 | 10/2004 | Gill et al. | |
| 2004/0215162 A1 | 10/2004 | Putz | |
| 2004/0249261 A1 | 12/2004 | Torchia et al. | |

(56) References Cited

U.S. PATENT DOCUMENTS

| | | |
|---|---|---|
| 2005/0004504 A1 | 1/2005 | Frye et al. |
| 2005/0112065 A1 | 5/2005 | Drummond et al. |
| 2005/0148865 A1* | 7/2005 | Weber .................. A61B 5/055 |
| | | 600/423 |
| 2005/0154297 A1 | 7/2005 | Gill |
| 2005/0256503 A1 | 11/2005 | Hall |
| 2006/0052750 A1* | 3/2006 | Lenker ............... A61B 17/3439 |
| | | 604/164.01 |
| 2006/0073101 A1 | 4/2006 | Oldfield et al. |
| 2006/0129126 A1 | 6/2006 | Kaplitt et al. |
| 2006/0135945 A1 | 6/2006 | Bankiewicz et al. |
| 2006/0217664 A1 | 9/2006 | Hattler et al. |
| 2007/0088295 A1 | 4/2007 | Bankiewicz |
| 2007/0110798 A1 | 5/2007 | Drummond et al. |
| 2007/0179455 A1 | 8/2007 | Geliebter et al. |
| 2007/0250021 A1 | 10/2007 | Brimhall et al. |
| 2007/0254842 A1 | 11/2007 | Bankiewicz |
| 2008/0119821 A1 | 5/2008 | Agnihotri et al. |
| 2008/0215008 A1 | 9/2008 | Nance et al. |
| 2008/0228168 A1 | 9/2008 | Mittermeyer et al. |
| 2009/0088695 A1 | 4/2009 | Kapur et al. |
| 2009/0088730 A1 | 4/2009 | Hoofnagle et al. |
| 2009/0112084 A1 | 4/2009 | Piferi et al. |
| 2009/0118610 A1 | 5/2009 | Karmarkar et al. |
| 2009/0143764 A1 | 6/2009 | Nelson |
| 2009/0171184 A1 | 7/2009 | Jenkins et al. |
| 2009/0198218 A1 | 8/2009 | Gill et al. |
| 2009/0209937 A1 | 8/2009 | Rogawski et al. |
| 2009/0281453 A1 | 11/2009 | Tsonton et al. |
| 2010/0130958 A1 | 5/2010 | Kang et al. |
| 2010/0198052 A1 | 8/2010 | Jenkins et al. |
| 2010/0217236 A1 | 8/2010 | Gill et al. |
| 2010/0317961 A1 | 12/2010 | Jenkins et al. |
| 2010/0318061 A1 | 12/2010 | Derrick et al. |
| 2010/0318064 A1 | 12/2010 | Derrick et al. |
| 2011/0282319 A1 | 11/2011 | Gill |
| 2012/0123391 A1 | 5/2012 | Gill et al. |
| 2012/0310182 A1 | 12/2012 | Fielder et al. |
| 2013/0030408 A1 | 1/2013 | Piferi et al. |
| 2014/0257168 A1 | 9/2014 | Gill |
| 2014/0343500 A1 | 11/2014 | Fielder et al. |
| 2016/0346505 A1 | 12/2016 | Gill et al. |

FOREIGN PATENT DOCUMENTS

| | | |
|---|---|---|
| EP | 1482851 A1 | 12/2004 |
| GB | 1255551 A | 12/1971 |
| JP | 2002509767 A | 4/2002 |
| JP | 2004-147830 A | 5/2004 |
| WO | WO 99/04849 A1 | 2/1999 |
| WO | WO 99/49909 A3 | 10/1999 |
| WO | WO 02/053205 A2 | 7/2002 |
| WO | WO 03/077785 A1 | 9/2003 |
| WO | WO 2004/031348 A1 | 4/2004 |
| WO | WO 2008/020237 A2 | 2/2008 |
| WO | WO 2008/020241 A2 | 2/2008 |
| WO | WO 2008/144585 | 11/2008 |
| WO | WO 2008/144775 A1 | 11/2008 |
| WO | WO 2009/042135 A2 | 4/2009 |
| WO | WO 2009/047490 A2 | 4/2009 |
| WO | WO 2009/066130 A1 | 5/2009 |
| WO | WO 2009/101397 A1 | 8/2009 |
| WO | WO 2010/040970 A2 | 4/2010 |
| WO | WO 2011/098768 A1 | 8/2011 |
| WO | WO 2011/098769 A1 | 8/2011 |
| WO | WO 2012/178169 A2 | 12/2012 |
| WO | WO 2013/050148 A1 | 4/2013 |
| WO | WO 2014/089373 A1 | 6/2014 |

OTHER PUBLICATIONS

Chen M.Y. et al., "Variables affecting convection-enhanced delivery to the striatum: a systematic examination of rate of infusion, cannula size, infusate concentration, and tissue-cannula sealing time", *J Neurosurg*, 90:315-320, 1999.

Chen T.C. et al., "Combination Therapy with Irinotecan and Protein Kinase C Inhibitors in Malignant Glioma", *Cancer*, 2003; 97(9 Suppl):2363-73.

Cunningham J. et al., "Distribution of AAV-TK following intracranial convection-enhanced delivery into rats", *Cell Transplant*, Sep.-Oct. 2000; 9(5):585-94, (Abstract Only).

Groothuis D. "The blood-brain and blood-tumor barriers: A review of strategies for increasing drug delivery", *Neuro-Oncology*, Jan. 2000, vol. 2, 45-49.

Hadaczek P. et al., "Convection-Enhanced Delivery of Adeno-Associated Virus Type 2 (AAV2) into the Striatum and Transport of AAV2 Within Monkey Brain", *Human Gene Therapy*, Mar. 2006, 17:291-302.

Hadaczek P. et al., "The "Perivascular Pump" Driven by Arterial Pulsation is a Powerful Mechanism for the Distribution of Therapeutic molecules within the Brain", *Molecular Therapy*, Jul. 2006, vol. 14, No. 1, 69-78.

Krauze M.T. et al., "Real-time Imaging and Quantification of Brain Delivery of Liposomes", *Pharmaceutical Research*, Nov. 2006, vol. 23, No. 11, 2493-2504.

Krauze M.T. et al., "Reflux-free cannula for convection-enhanced high-speed delivery of therapeutic agents", *J Neurosurg*, 103:923-929, 2005.

Laske D.W. et al., "Chronic interstitial infusion of protein to primate brain: determination of drug distribution and clearance with single-photon emission computerized tomography imaging", *J Neurosurg*, 87:586-594, 1997.

Lieberman D.M. et al., "Convection-enhanced distribution of large molecules in gray matter during interstitial drug infusion", *J Neurosurg*, 82:1021-1029, 1995.

Lonser R.R. et al., "Successful and safe perfusion of the primate brainstem: in vivo magnetic resonance imaging of macromolecular distribution during infusion", *J Neurosurg*, 97:905-913, 2002.

Mamot C. et al., "Extensive distribution of liposomes in rodent brains and brain tumors following convection-enhanced delivery", *Journal of Neuro-Oncology*, 68: 1-9, 2004.

Mardor Y. et al., "Monitoring Response to Convection-enhanced Taxol Delivery in Brain Tumor Patients Using Diffusion-weighted Magnetic Resonance Imaging", *Cancer Res*, 2001;61:4971-4973.

Marshall D.J. et al., "Biocompatibility of Cardiovascular Gene Delivery Catheters with Adenovirus Vectors: An Important Determinant of the Efficiency of Cardiovascular Gene Transfer", *Molecular Therapy*, vol. 1, No. 5, May 2000, 423-429.

Morrison P.F. et al., "Focal delivery during direct infusion to brain: role of flow rate, catheter diameter, and tissue mechanics", *Am J Physiol Regul Integr Comp Physiol*, 277:R1218-R1229, 1999.

Morrison P.F. et al., "High-flow microinfusion: tissue penetration and pharmacodynamics", *Am J Physiol Regul Integr Comp Physiol*, 266:R292-R305, 1994.

Naimark W.A. et al., "Adenovirus-Catheter Compatibility Increases Gene Expression After Delivery to Porcine Myocardium", *Human Gene Therapy*, 14:161-166, Jan. 20, 2003.

Pardridge W.M. "Drug Delivery to the Brain", *Journal of Cerebral Blood Flow and Metabolism*, 1997, 17:713-731.

Pardridge W.M. "The Blood-Brain Barrier: Bottleneck in Brain Drug Development", *NeuroRx: The Journal of the American Society for Experimental NeuroTherapeutics*, Jan. 2005, vol. 2, 3-14.

Patel N.K. et al., "Intraputamenal Infusion of Glial Cell Line-Derived Neurotrophic Factor in PD: A Two-Year Outcome Study", *Annals of Neurology*, Feb. 2005, vol. 57, No. 2, 298-302.

Qureshi N.H. et al., "Multicolumn Infusion of Gene Therapy Cells into Human Brain Tumors: Technical Report", *Neurosurgery*, Mar. 2000, vol. 46, Issue 3, pp. 663-669 (Abstract Only).

Richardson R. Mark et al., "Interventional MRI-guided Putaminal Delivery of AAV2-GDNF for a Planned Clinical Trial in Parkinson's Disease", *Molecular Therapy*, Jun. 2011, 19(6).

Rogawski M.A. et al., "Convection-Enhanced Delivery in the Treatment of Epilepsy", *Neurotherapeutics: The Journal of the American Society for Experimental Neuro Therapeutics*, vol. 6, 344-351, Apr. 2009.

(56) References Cited

OTHER PUBLICATIONS

Saito R. et al., "Convection-Enhanced Delivery of Tumor Necrosis Factor-Related Apoptosis-Inducing Ligand with Systemic Administration of Temozolomide Prolongs Survival in an Intracranial Glioblastoma Xenograft Model", *Cancer Res*, 2004;64:6858-6862.
Saito R. et al., "Distribution of Liposomes into Brain and Rat Brain Tumor Models by Convection-Enhanced Delivery Monitored with Magnetic Resonance Imaging", *Cancer Res*, 2004;64:2572-2579.
Tsui L.V. et al., "Stability of Adenoviral Vectors Following Catheter Delivery", *Molecular Therapy*, vol. 3, No. 1, Jan. 2001, 122-125.
Vogelbaum M.A. et al., "Convection enhanced delivery for the treatment of malignant gliomas: symposium review",*Journal of Neuro-Oncology*, 2005, 73: 57-69.
Westphal m. et al., "Perspectives of cellular and molecular neurosurgery", *Journal of Neuro-Oncology*, 2004, 70: 255-269.
Bankiewicz et al., "Convection-Enhanced Delivery of AAV Vector in Parkinsonian Monkeys; in Vivo Detection of Gene Expression and Restoration of Dopaminergic Function Using Pro-drug Approach", *Experimental Neurology*, 164, 2-14 (2000).
Extended European Search Report Corresponding to European Application No. 11769340.8 dated Dec. 9, 2016; 7 Pages.

\* cited by examiner

MRI SURGICAL SYSTEMS INCLUDING MRI-COMPATIBLE SURGICAL CANNULAE FOR TRANSFERRING A SUBSTANCE TO AND/OR FROM A PATIENT

RELATED APPLICATION INFORMATION

This application is a 35 U.S.C. § 371 national stage filing of PCT International Application No. PCT/US2011/031678, filed Apr. 8, 2011, which claims the benefit of U.S. Provisional Patent Application No. 61/324,990, filed Apr. 16, 2010, the disclosures of which are incorporated herein by reference in their entireties.

FIELD OF THE INVENTION

The present invention relates to MRI-guided diagnostic or interventional systems that may be particularly suitable for placement/localization of therapies in the body.

BACKGROUND OF THE INVENTION

Various therapeutic and diagnostic procedures require that a substance be infused into a prescribed region of a patient, such as into a target deep brain location in the patient's brain, using a delivery cannula. It is often important or critical that the substance be delivered with high accuracy to the target region in the patient and without undue trauma to the patient. Moreover, it may be desirable to control or alter aspects of the flow of the substance into the target region from the delivery cannula.

SUMMARY OF THE INVENTION

According to embodiments of the present invention, a cannula for transferring a substance to and/or from a patient includes a tubular support sleeve and a transfer tube. The support sleeve includes a rigid tubular member defining a lumen extending from a proximal end to a distal end of the tubular member. The transfer tube is positioned in the lumen and extends beyond each of the proximal end and the distal end of the tubular member. The tubular member comprises a rigid, MRI-compatible material.

According to some embodiments, the tubular member comprises a ceramic material.

In some embodiments, the cannula includes a conformal polymeric sleeve surrounding the tubular member. According to some embodiments, the conformal polymeric sleeve is a polymeric shrink tubing.

According to some embodiments, an exterior surface of the cannula has at least first and second co-axially disposed segments having different outer diameters. In some embodiments, the exterior surface includes a tapered transition between the first and second segments.

The cannula may include a second tubular member disposed in the first tubular member and extending beyond the distal end of the first tubular member, wherein the transfer tube extends beyond a distal end of the second tubular member.

In some embodiments, the transfer tube is formed of fused silica.

According to some embodiments, the tubular member has a length of at least 10 inches.

In some embodiments, an outer surface of the tubular member has a size and geometry adapted for use with a stereotactic frame.

According to embodiments of the present invention, a cannula for transferring a substance to and/or from a patient includes a tubular support sleeve. The support sleeve includes a rigid tubular member defining a lumen extending from a proximal end to a distal end of the tubular member. An exterior surface of the cannula has at least first and second co-axially disposed segments having different outer diameters. The tubular member comprises a ceramic material.

According to method embodiments of the present invention, a method of transferring a substance to and/or from a patient includes: providing a cannula including a rigid tubular member defining a lumen, wherein the tubular member comprises a ceramic material; inserting the cannula into a selected region in the patient; and transferring the substance to or from the selected region through the lumen.

In some embodiments, the selected region is the brain.

According to embodiments of the present invention, a cannula for transferring a substance to and/or from a patient includes a rigid tubular support sleeve defining a lumen extending from a proximal end to a distal end thereof. An exterior surface of the cannula has at least first and second co-axially disposed segments having different outer diameters. The exterior surface includes a tapered transition between the first and second segments.

According to embodiments of the present invention, a cannula for transferring a substance to and/or from a patient includes a rigid tubular support sleeve and a transfer tube. The support sleeve defines a lumen extending from a proximal end to a distal end thereof. The transfer tube is positioned in the lumen and extends beyond each of the proximal end and the distal end of the tubular support sleeve. The transfer tube has an inner diameter of about 200 micrometers.

According to embodiments of the present invention, a cannula for transferring a substance to and/or from a patient defines a lumen extending from a proximal end to a distal end thereof. An exterior surface of the cannula has at least first, second and third co-axially disposed segments having different outer diameters, the outer diameter of the second segment being greater than the outer diameter of the first segment and the outer diameter of the third segment being greater than the outer diameter of the second segment. The first segment extends from the distal terminus of the cannula from which the substance is dispensed in use. The second segment extends between and adjoins each of the first and third segments. The length of the second segment is about 15 mm.

According to embodiments of the present invention, a cannula for transferring a substance to and/or from a patient includes a rigid tubular support sleeve, a transfer tube, and silicone or PVC protective tubing. The support sleeve defines a lumen extending from a proximal end to a distal end thereof. The transfer tube is positioned in the lumen and extends beyond each of the proximal end and the distal end of the tubular support sleeve. The protective tubing extends from the proximal end of the tubular support sleeve and surrounds the portion of the transfer tube extending beyond the proximal end of the tubular support sleeve.

According to embodiments of the present invention, an MRI-guided surgical system for delivering a substance to a patient includes an MRI-compatible delivery cannula, a circuit and at least one display. The delivery cannula is configured to deliver the substance to a selected region in the patient. The circuit is adapted to communicate with an MRI scanner. The circuit automatically segments MR image data provided by the MRI scanner. The at least one display is in communication with the circuit. The circuit is configured to generate and display visualizations of the substance registered to patient anatomical structure in near real-time to facilitate the MRI-guided surgical procedure.

According to method embodiments of the present invention, a method for delivering a substance to a patient in an MRI-guided surgical procedure includes: delivering the substance to a selected region in the patient using an MRI-compatible delivery cannula; obtaining MRI image data of the patient; automatically segmenting the MRI image data; and generating and displaying visualizations of the delivered substance registered to patient anatomical structure in near real-time. The visualizations facilitate the MRI-guided surgical procedure.

According to some embodiments, the step of generating and displaying visualizations of the delivered substance registered to the patient anatomical structure in near real-time includes visually showing a dynamic dispersion and/or infusion pattern.

According to embodiments of the present invention, an MRI-guided surgical system for transferring a substance to and/or from a patient includes an MRI-compatible cannula, a circuit and at least one display. The MRI-compatible cannula is configured to transfer the substance to or from a selected region in the patient. The circuit is adapted to communicate with an MRI scanner. The circuit automatically segments MR image data provided by the MRI scanner. The at least one display is in communication with the circuit. The circuit is configured to generate and display visualizations of the cannula registered to patient anatomical structure in near real-time to facilitate the MRI-guided surgical procedure.

According to some embodiments, the circuit is configured to generate and display visualizations of the delivered substance registered to the patient anatomical structure in near real-time to visually show a dynamic dispersion and/or infusion pattern of the delivered substance.

According to embodiments of the present invention, a method for transferring a substance to and/or from a patient in an MRI-guided surgical procedure includes: transferring the substance to or from a selected region in the patient using an MRI-compatible cannula; obtaining MRI image data of the patient; automatically segmenting the MRI image data; and generating and displaying visualizations of the cannula registered to patient anatomical structure in near real-time. The visualizations facilitate the MRI-guided surgical procedure.

According to embodiments of the present invention, an MRI-guided surgical system for transferring a substance to and/or from a patient includes an MRI-compatible cannula, a circuit, and at least one display. The MRI-compatible cannula is configured to transfer the substance to or from a selected region in the patient. The cannula includes an adjustment feature to selectively vary at least one characteristic of the flow of the substance dispensed from or drawn into the cannula. The circuit is adapted to communicate with an MRI scanner. The at least one display is in communication with the circuit. The circuit is configured to generate and display visualizations of the cannula and/or the substance in near real-time to facilitate the MRI-guided surgical procedure.

In some embodiments, the cannula has predefined physical characteristics known to the circuit and/or an operator and which can be used to assess a setting of the adjustment feature. According to some embodiments, the circuit electronically recognizes the predefined physical characteristics of the cannula and is operable to evaluate MR image data from the MRI scanner to assess the setting of the adjustment feature.

According to some embodiments, the circuit is configured to electronically generate directions on adjustments to the cannula using the adjustment feature to obtain a new setting of the adjustment feature.

In some embodiments, the at least one characteristic of the flow of the substance dispensed from or drawn into the cannula includes a flow rate and/or a flow pattern of the flow of the substance dispensed from the delivery cannula.

According to method embodiments of the present invention, a method for delivering a substance to a patient in an MRI-guided surgical procedure includes: delivering the substance to a selected region in the patient using an MRI-compatible delivery cannula, the delivery cannula including an adjustment feature; obtaining MR image data of the patient; and adjusting at least one characteristic of the flow of the substance dispensed from the delivery cannula using the adjustment feature and the MR image data.

In some embodiments, the foregoing method includes generating and displaying visualizations of the delivery cannula and/or the substance in near real-time to facilitate the MRI-guided surgical procedure.

According to method embodiments of the present invention, a method for transferring a substance to and/or from a patient in an MRI-guided surgical procedure includes: mounting an MRI-compatible intrabody surgical cannula on an MRI-compatible guide frame; selectively positioning the intrabody surgical cannula with respect to the patient using the guide frame; obtaining MRI image data of the patient; and generating and displaying visualizations of the intrabody surgical cannula and/or the guide frame registered to patient anatomical structure, wherein the visualizations facilitate the MRI-guided surgical procedure.

In some embodiments, the method includes delivering the substance through the intrabody surgical cannula into the patient.

DETAILED DESCRIPTION OF EMBODIMENTS OF THE INVENTION

Figure 1:
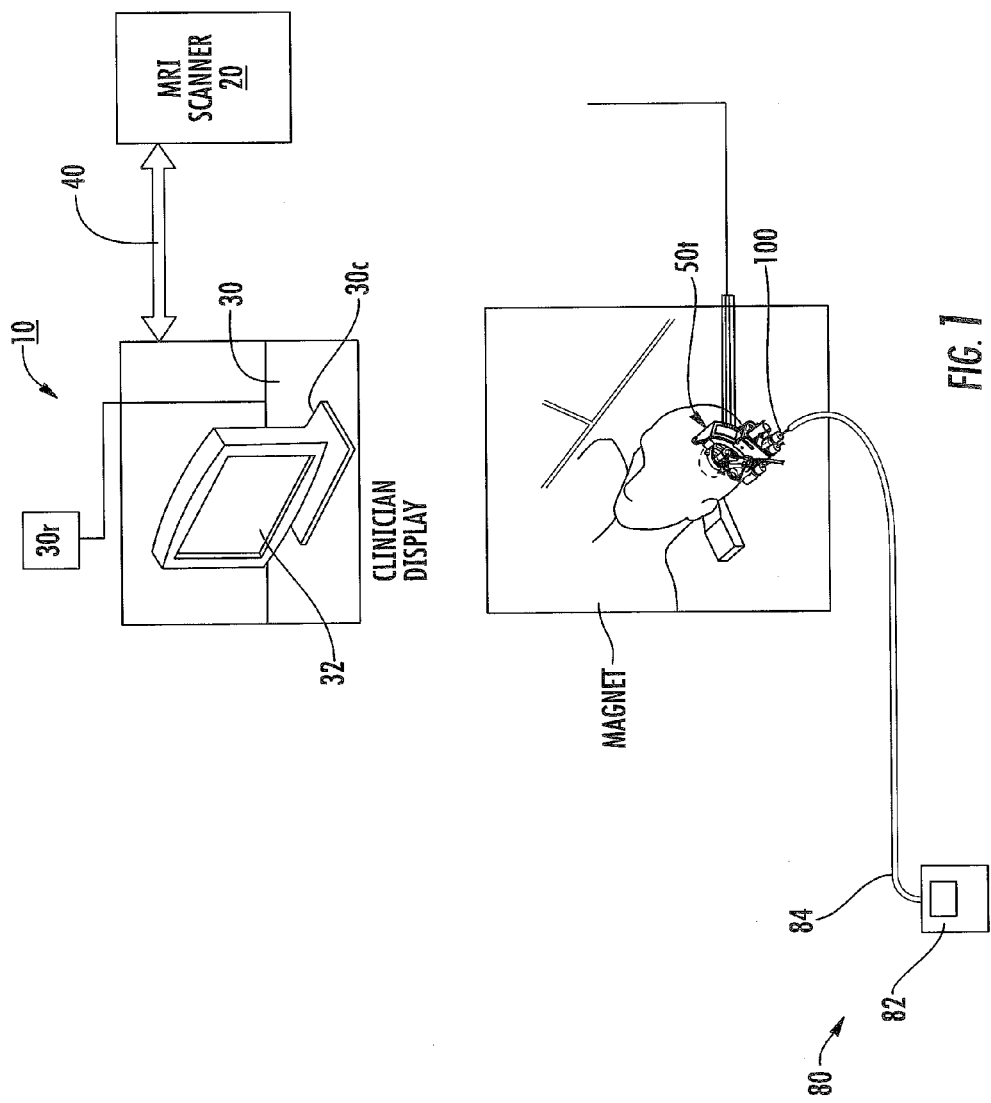
FIG. 1 is a schematic illustration of a MRI-guided surgical system according to some embodiments of the present invention.

The present invention will now be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. It will be appreciated that although discussed with respect to a certain embodiment, features or operation of one embodiment can apply to others.

In the drawings, the thickness of lines, layers, features, components and/or regions may be exaggerated for clarity and broken lines (such as those shown in circuit of flow diagrams) illustrate optional features or operations, unless specified otherwise. In addition, the sequence of operations (or steps) is not limited to the order presented in the claims unless specifically indicated otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when a feature, such as a layer, region or substrate, is referred to as being "on" another feature or element, it can be directly on the other element or intervening elements may also be present. In contrast, when an element is referred to as being "directly on" another feature or element, there are no intervening elements present. It will also be understood that, when a feature or element is referred to as being "connected" or "coupled" to another feature or element, it can be directly connected to the other element or intervening elements may be present. In contrast, when a feature or element is referred to as being "directly connected" or "directly coupled" to another element, there are no intervening elements present. Although described or shown with respect to one embodiment, the features so described or shown can apply to other embodiments.

The term "electroanatomical visualization" refers to a visualization or map of the anatomical structure, e.g., brain, typically a volumetric, 3-D map or 4-D map, that illustrates or shows electrical activity of tissue correlated to anatomical and/or coordinate spatial position. The visualization can be in color and color-coded to provide an easy to understand map or image with different measures or gradients of activity in different colors and/or intensities. The term "color-coded" means that certain features, electrical activity or other output are shown with defined colors of different color and/or intensity to visually accentuate different tissue, different and similar electrical activity or potential in tissue and/or to show abnormalities or lesions in tissue versus normal or non-lesion tissue. In some embodiments, the systems can be configured to allow a clinician to increase or decrease the intensity or change a color of certain tissue types or electrical outputs, e.g., in high-contrast color and/or intensity, darker opacity or the like.

The actual visualization can be shown on a screen or display so that the map and/or anatomical or tool structure is in a flat 2-D view and/or in 2-D what appears to be 3-D volumetric images with data representing features or electrical output with different visual characteristics such as with differing intensity, opacity, color, texture and the like. For example, the 3-D image of the lung can be generated to illustrate differences in barrier thickness using color or opacity differences over the image volume. Thus, the term "3-D" in relation to images does not require actual 3-D viewability (such as with 3-D glasses), just a 3-D appearance, typically on a display. The 3-D images comprise multiple 2-D slices. The 3-D images can be volume renderings well known to those of skill in the art and/or a series of 2-D slices, which can be visually paged through. A 4-D map illustrates time-dependent activity, such as electrical activity or blood flow movement.

The surgical systems may be configured to operate based on known physical characteristics of one or more surgical tools, which may include a surgical (e.g., delivery) cannula, such that the hardware is a point of interface for the circuit or software. The systems can communicate with databases that define dimensions, configurations or shapes and spacing of components on the tool(s). The defined physical data can be obtained from a CAD model of a tool. The physical characteristics can include dimensions or other physical features or attributes and may also include relative changes in position of certain components or features upon a change in position of a tool or portion thereof. The defined physical characteristics can be electronically (programmatically) accessible by the system or known a priori and electronically stored locally or remotely and used to automatically calculate certain information and/or to segment image data. That is, tool data from the known dimensions and configuration of the tool model can be used to segment image data and/or correlate a position and orientation of a tool and/or provide trajectory adjustment guidelines or error estimates, warnings of improper trajectories and the like. For example, the system can include defined structural and/or operational details/data for one or more of a delivery cannula, a grid for marking a burr hole location and/or a trajectory guide. The system can use this data to allow a user to adjust an intrabrain path for placing a diagnostic or therapy device. Such can be input, transposed, and/or overlayed in a visualization of the tool on one or more displays along with patient structure or otherwise used, such as, for example, to project the information onto a patient's anatomical structure or determine certain operational parameters including which image volume (scan planes) to use to obtain MRI image data that will include select portions of the targeting cannula or surgical cannula. As such, at least some of the generated visualizations are not merely an MRI image of the patient during a procedure.

The visualizations are rendered visualizations that can combine multiple sources of data to provide visualizations of spatially encoded tool position and orientation with anatomical structure and can be used to provide position adjustment data output so that a clinician can obtain a desired trajectory path, thereby providing a smart-adjustment system without requiring undue "guess" work on what adjustments to make to obtain the desired trajectory.

The term "animation" refers to a sequence or series of images shown in succession, typically in relatively quick succession, such as in about 1-50 frames per second. The term "frame" refers to a single visualization or static image. The term "animation frame" refers to one image frame of the different images in the sequence of images.

The term "ACPC coordinate space" refers to a right-handed coordinate system defined by anterior and posterior commissures (AC, PC) and Mid-Sagittal plane points, with positive directions corresponding to a patient's anatomical Right, Anterior and Head directions with origin at the mid-commissure point.

The term "grid" refers to a pattern of crossed lines or shapes used as a reference for locating points or small spaces, e.g., a series of rows and intersecting columns, such as horizontal rows and vertical columns (but orientations other than vertical and horizontal can also be used). The grid can include associated visual indicia such as alphabetical markings (e.g., A-Z and the like) for rows and numbers for columns (e.g., 1-10) or the reverse. Other marking indicia may also be used. The grid can be provided as a flexible patch that can be releasably attached to the skull of a patient. For additional description of suitable grid devices, see co-pending, co-assigned U.S. patent application Ser. No. 12/236,621 (U.S. Published Patent Application No. US-2009-00177077-A1), the disclosure of which is incorporated herein by reference.

The term "fiducial marker" refers to a marker that can be electronically identified using image recognition and/or electronic interrogation of MRI image data. The fiducial marker can be provided in any suitable manner, such as, but not limited to, a geometric shape of a portion of the tool, a component on or in the tool, a coating or fluid-filled component or feature (or combinations of different types of fiducial markers) that makes the fiducial marker(s) MRI-visible with sufficient signal intensity (brightness) or generates a "void" or dark space for identifying location and/or orientation information for the tool and/or components thereof in space.

The term "MRI scanner" refers to a magnetic resonance imaging and/or NMR spectroscopy system. As is well known, MRI scanners include a low field strength magnet (typically between about 0.1 T to about 0.5 T), a medium field strength magnet, or a high-field strength super-conducting magnet, an RF pulse excitation system, and a gradient field system. MRI scanners are well known to those of skill in the art. Examples of commercially available clinical MRI scanners include, for example, those provided by General Electric Medical Systems, Siemens, Philips, Varian, Bruker, Marconi, Hitachi and Toshiba. The MRI systems can be any suitable magnetic field strength, such as, for example, about 1.5 T or about 3.0 T, and may include other high-magnetic field systems between about 2.0 T-10.0 T.

The term "RF safe" means that the lead or probe is configured to safely operate when exposed to RF signals, particularly RF signals associated with MRI systems, without inducing unplanned current that inadvertently unduly heats local tissue or interferes with the planned therapy.

The term "MRI visible" means that the device is visible, directly or indirectly, in an MRI image. The visibility may be indicated by the increased SNR of the MRI signal proximate the device.

The term "MRI compatible" means that the so-called component(s) is suitable for use in an MRI environment and as such is typically made of a non-ferromagnetic MRI compatible material(s) suitable to reside and/or operate in or proximate a conventional medical high magnetic field environment. The "MRI compatible" component or device is "MR safe" when used in the MRI environment and has been demonstrated to neither significantly affect the quality of the diagnostic information nor have its operations affected by the MR system at the intended use position in an MR system. These components or devices may meet the standards defined by ASTM F2503-05. See, American Society for Testing and Materials (ASTM) International, Designation: F2503-05. Standard Practice for Marking Medical Devices and Other Items for Safety in the Magnetic Resonance Environment. ASTM International, West Conshohocken, Pa., 2005.

The term "near real time" refers to both low latency and high frame rate. Latency is generally measured as the time from when an event occurs to display of the event (total processing time). For tracking, the frame rate can range from between about 100 fps to the imaging frame rate. In some embodiments, the tracking is updated at the imaging frame rate. For near 'real-time' imaging, the frame rate is typically between about 1 fps to about 20 fps, and in some embodiments, between about 3 fps to about 7 fps. The low latency required to be considered "near real time" is generally less than or equal to about 1 second. In some embodiments, the latency for tracking information is about 0.01 s, and typically between about 0.25-0.5 s when interleaved with imaging data. Thus, with respect to tracking, visualizations with the location, orientation and/or configuration of a known intrabody device can be updated with low latency between about 1 fps to about 100 fps. With respect to imaging, visualizations using near real time MR image data can be presented with a low latency, typically within in between about 0.01 ms to less than about 1 second, and with a frame rate that is typically between about 1-20 fps. Together, the system can use the tracking signal and image signal data to dynamically present anatomy and one or more intrabody devices in the visualization in near real-time. In some embodiments, the tracking signal data is obtained and the associated spatial coordinates are determined while the MR image data is obtained and the resultant visualization(s) with the intrabody device (e.g., surgical cannula) and the near RT MR image(s) are generated.

The term "automatically" means that the operation can be substantially, and typically entirely, carried out without human or manual input, and is typically programmatically directed or carried out. The term "electronically" includes both wireless and wired connections between components. The term "programmatically" means under the direction of a computer program that communicates with electronic circuits and other hardware and/or software.

The term "surgical cannula" refers to an intrabody cannula used to transfer a substance to and/or from a target intrabody location.

Embodiments of the invention may be particularly suitable for use with human patients but may also be used with any animal or other mammalian subject.

Embodiments of the present invention may take the form of an entirely software embodiment or an embodiment combining software and hardware aspects, all generally referred to herein as a "circuit" or "module." In some embodiments, the circuits include both software and hardware and the software is configured to work with specific hardware with known physical attributes and/or configurations. Furthermore, the present invention may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or other storage devices.

Computer program code for carrying out operations of the present invention may be written in an object oriented programming language such as Java®, Smalltalk or C++. However, the computer program code for carrying out operations of the present invention may also be written in conventional procedural programming languages, such as the "C" programming language. The program code may execute entirely on the user's computer, partly on the user's computer, as a stand-alone software package, partly on the user's computer and partly on another computer, local and/or remote or entirely on the other local or remote computer. In the latter scenario, the other local or remote computer may be connected to the user's computer through a local area network (LAN) or a wide area network (WAN), or the connection may be made to an external computer (for example, through the Internet using an Internet Service Provider).

Embodiments are described in part below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

The flowcharts and block diagrams of certain of the figures herein illustrate exemplary architecture, functionality, and operation of possible implementations of embodiments of the present invention. In this regard, each block in the flow charts or block diagrams represents a module, segment, or portion of code, which comprises one or more executable instructions for implementing the specified logical function(s). It should also be noted that in some alternative implementations, the functions noted in the blocks may occur out of the order noted in, the figures. For example, two blocks shown in succession may in fact be executed substantially concurrently or the blocks may sometimes be executed in the reverse order or two or more blocks may be combined, depending upon the functionality involved.

Some embodiments of the present invention are directed to MRI-guided systems that can generate substantially real time (e.g., near real-time) patient-specific visualizations of the patient and one or more surgical tools, including an MRI-compatible intrabody surgical cannula (e.g., delivery cannula) and the delivery distribution, location, pattern, etc., in logical space and provide feedback to a clinician to improve the speed and/or reliability of an intrabody infusion or delivery of a substance to a target within the body through the delivery cannula. The delivery cannula has at least one lumen and at least one exit port configured to direct a flow of the substance through the lumen and the exit port to the target.

Some embodiments of the present invention are directed to MRI-guided systems that can generate substantially real time patient-specific visualizations of the patient and a distribution of a substance delivered to a target within the patient through an MRI-compatible delivery cannula in logical space and provide feedback to a clinician to improve the speed and/or reliability of an intrabody infusion or delivery of the substance. These systems can show a dynamic dispersion and/or infusion pattern of the substance infused into the patient. MRI can be effectively used to monitor the efficacy and/or delivery of the substance from the delivery cannula.

The visualizations can be based (in-part) on predefined data of the delivery cannula which can define a point of interface for the system (e.g., software) based on predefined characteristics of the delivery cannula, e.g., dimensions, shape or configuration and/or known rotational, translational and/or other functional and/or dynamic behavior of the delivery cannula (e.g., flow rate, nozzle angle). The visualizations can include patient function data (e.g., fMRI data, electrical activity, active regions of a brain during a defined stimulation, fiber tracks, and the like).

The system can be configured to interrogate and segment image data to locate fiducial markers in the image (e.g., an increased higher intensity pixel/voxel region and/or void created in the MRI image by the presence of the delivery cannula in the patient's tissue) and generate successive visualizations of the patient's anatomical structure and the delivery cannula using MRI image data and a priori data of the delivery cannula to provide (substantially real-time) visualizations of the distribution of the substance in the patient.

Some embodiments of the present invention can provide visualizations to allow more precise control, delivery, and/or feedback of an infusion therapy so that the therapy or delivery cannula associated therewith can be more precisely placed and/or so that the cannula or delivery can be adjusted to provide the desired distribution in tissue, or to confirm proper delivery and allow near real-time visualization of the procedure.

Some embodiments of the present invention are directed to reflux-resistant, MRI-compatible intrabody delivery cannulae.

Some embodiments of the present invention are directed to MRI-compatible intrabody delivery cannulae including mechanisms that allow an operator to selectively adjust a flow rate, port size, port number or other components that adjust distribution of a substance delivered through the cannula to a target within the patient.

The delivery cannula may be used to precisely deliver any suitable and desired substance (e.g., cellular, biological, and/or drug therapeutics) to the desired anatomy target. The delivery cannulae can be used in and the systems can be configured to guide and/or place the delivery cannula in any desired internal region of the body of the patient, but may be particularly suitable for neurosurgeries and delivery of a substance to a target area or region within the brain. The delivery cannulae and systems can be used for gene and/or stem-cell based therapy delivery or other neural therapy delivery and allow user-defined custom targets in the brain or to other locations. Cannulae, systems and methods of the invention may be used to treat patients by delivery of cellular/biological therapeutics into the desired anatomy to modify their cellular function. The cells (e.g., stem cells) may improve function.

The target region may be any suitable region or area within the patient body. According to some embodiments, the target region is a STN anatomical region, which may be identified and located with reference to standard anatomical landmarks. According to some embodiments, the target area is a deep brain tumor or other undesirable tissue mass.

According to some embodiments, the target is intrathecal. The intrathecal target may be in the brain or spinal cord.

The substance delivered to the target region through the delivery cannula may be any suitable and desired substance. According to some embodiments, the substance is a liquid or slurry. In the case of a tumor, the substance may be a chemotherapeutic (cytotoxic) fluid. In some embodiments, the substance can include certain types of advantageous cells that act as vaccines or other medicaments (for example, antigen presenting cells such as dentritic cells). The dentritic cells may be pulsed with one or more antigens and/or with RNA encoding one or more antigen. Exemplary antigens are tumor-specific or pathogen-specific antigens. Examples of tumor-specific antigens include, but are not limited to, antigens from tumors such as renal cell tumors, melanoma, leukemia, myeloma, breast cancer, prostate cancer, ovarian cancer, lung cancer and bladder cancer. Examples of pathogen-specific antigens include, but are not limited to, antigens specific for HIV or HCV. In some embodiments, the substance may comprise radioactive material such as radioactive seeds. Substances delivered to a target area may include, but are not limited to, the following as shown in Table 1:

TABLE 1

| DRUG (generic name) | DISORDER(S) |
| --- | --- |
| caprylidene | Alzheimer's disease |
| donepezil | Alzheimer's disease |
| galantamine | Alzheimer's disease |
| memantine | Alzheimer's disease |
| Tacrine | Alzheimer's disease |
| vitamin E | Alzheimer's disease |
| ergoloid mesylates | Alzheimer's disease |
| riluzole | Amyotrophic lateral sclerosis |
| metoprolol | Benign essential tremors |
| primidone | Benign essential tremors |
| propanolol | Benign essential tremors |
| gabapentin | Benign essential tremors & Epilepsy |
| nadolol | Benign essential tremors & Parkinson's disease |
| zonisamide | Benign essential tremors & Parkinson's disease |
| carmustine | Brain tumor |
| lomustine | Brain tumor |
| methotrexate | Brain tumor |
| cisplatin | Brain tumor & Neuroblastoma |
| ioversol | Cerebral arteriography |
| mannitol | Cerebral Edema |
| dexamethasone | Cerebral Edema & Neurosarcoidosis |
| baclofen | Cerebral spasticity |
| ticlopidine | Cerebral thrombosis/embolism |
| isoxsuprine | Cerebrovascular insufficiency |
| cefotaxime | CNS infection & Meningitis |
| acyclovir | Encephalitis |
| foscarnet | Encephalitis |
| ganciclovir | Encephalitis |
| interferon alpha-2a | Encephalitis |
| carbamazepine | Epilepsy |
| clonazepam | Epilepsy |
| diazepam | Epilepsy |
| divalproex sodium | Epilepsy |
| ethosuximide | Epilepsy |
| ethotoin | Epilepsy |
| felbamate | Epilepsy |
| fosphenytoin | Epilepsy |
| levetiracetam | Epilepsy |
| mephobarbital | Epilepsy |
| paramethadione | Epilepsy |
| phenytoin | Epilepsy |
| trimethadione | Epilepsy |
| pregabalin | Epilepsy & Neuralgia |
| immune globulin intravenous | Guillain-Barre Syndrome |
| interferon beta-1b | Guillain-Barre Syndrome & Multiple sclerosis |
| azathioprine | Guillain-Barre Syndrome & Multiple sclerosis & Neurosarcoidosis |
| risperidone | Head injury |
| tetrabenazine | Huntington's disease |
| acetazolamide | Hydrocephalus & Epilepsy |
| alteplase | Ischemic stroke |
| clopidogrel | Ischemic stroke |
| nimodipine | Ischemic stroke & Subarachnoid hemorrhage |
| Aspirin | Ischemic stroke & Thromboembolic stroke |
| amikacin | Encephalitis |
| ampicillin | Encephalitis |

TABLE 1-continued

| DRUG (generic name) | DISORDER(S) |
|---|---|
| ampicillin/sulbactam | Encaphalitis |
| ceftazidime | Encaphalitis |
| ceftizoxime | Encaphalitis |
| cefuroxime | Encaphalitis |
| chloramphenicol | Encaphalitis |
| cilastatin/imipenem | Encaphalitis |
| gentamicin | Encaphalitis |
| meropenem | Encaphalitis |
| metronidazole | Encaphalitis |
| nafcillin | Encaphalitis |
| oxacillin | Encaphalitis |
| piperacillin | Encaphalitis |
| rifampin | Encaphalitis |
| sulfamethoxazole/trimethoprim | Encaphalitis |
| tobramycin | Encaphalitis |
| triamcinolone | Encaphalitis |
| vancomycin | Encaphalitis |
| ceftriaxone | Encaphalitis & Neurosyphilis |
| pennicillin | Encaphalitis & Neurosyphilis |
| corticotropin | Multiple sclerosis |
| dalfampridine | Multiple sclerosis |
| glatiramer | Multiple sclerosis |
| mitoxantrone | Multiple sclerosis |
| natalizumab | Multiple sclerosis |
| modafinil | Multiple sclerosis |
| cyclophosphamide | Multiple sclerosis & Brain tumor & Neuroblastoma |
| interferon beta-1a | Multiple sclerosis & Neuritis |
| prednisolone | Multiple sclerosis & Neurosarcoidosis |
| prednisone | Multiple sclerosis & Neurosarcoidosis |
| amantadine | Multiple sclerosis & Parkinson's disease |
| methylprednisolone | Neuralgia |
| desvenlafaxine | Neuralgia |
| nortriptyline | Neuralgia |
| doxorubicin | Neuroblastoma |
| vincristine | Neuroblastoma |
| albendazole | Neurocystecercosis |
| chloroquine phosphate | Neurosarcoidosis |
| hydroxychloroquine | Neurosarcoidosis |
| infliximab | Neurosarcoidosis |
| pentoxyfilline | Neurosarcoidosis |
| thalidomide | Neurosarcoidosis |
| apomorphine | Parkinson's disease |
| belladonna | Parkinson's disease |
| benztropine | Parkinson's disease |
| biperiden | Parkinson's disease |
| bromocriptine | Parkinson's disease |
| carbidopa | Parkinson's disease |
| carbidopa/entacapone/levodopa | Parkinson's disease |
| carbidopa/levodopa | Parkinson's disease |
| entacapone | Parkinson's disease |
| levodopa | Parkinson's disease |
| pergolide mesylate | Parkinson's disease |
| pramipexole | Parkinson's disease |
| procyclidine | Parkinson's disease |
| rasagiline | Parkinson's disease |
| ropinirole | Parkinson's disease |
| rotiotine | Parkinson's disease |
| scopolamine | Parkinson's disease |
| tolcapone | Parkinson's disease |
| trihexyphenidyl | Parkinson's disease |
| seleginline | Parkinson's disease |
| rivastigmine | Parkinson's disease & Alzheimer's disease |
| anisindione | Thromboembolic stroke |
| warfarin | Thromboembolic stroke |
| 5-hydroxytryptophan | Depression & Anxiety & ADHD |
| duloxetine | Depression & Anxiety & Bipolar disorder |
| escitalopram | Depression & Anxiety & Bipolar disorder |
| venlafaxine | Depression & Anxiety & Bipolar disorder & Autism & Social anxiety disorder |
| desvenlafaxine | Depression & Anxiety & PTSD & ADHD |
| paroxetine | Depression & Anxiety & PTSD & Social anxiety disorder |
| fluoxetine/olanzapine | Depression & Bipolar disorder |
| l-methylfolate | Depression & BPD |
| amitriptyline | Depression & PTSD |
| sertraline | Depression & PTSD & Bipolar disorder & Social anxiety disorder |
| fluvoxamine | Depression & PTSD & Social anxiety disorder |
| olanzapine | Depression & Schizophrenia & Bipolar disorder |
| paliperidone | Depression & Schizophrenia & Bipolar disorder |
| aripiprazole | Depression & Schizophrenia & Bipolar disorder & Autism |
| quetiapine | Depression & Schizophrenia & PTSD & BPD & Bipolar disorder |
| risperidone | Depression & Schizophrenia & PTSD & BPD & Bipolar disorder & Autism |
| amisulpride | Depression & Social anxiety disorder |
| chlorpromazine | Psychosis |
| droperidol | Psychosis |
| fluphenazine | Psychosis |
| periciazine | Psychosis |
| perphenazine | Psychosis |
| thiothixene | Psychosis |
| triflupromazine | Psychosis |
| haloperidol | Psychosis & Dementia |
| prazosin | PTSD |
| clozapine | Schizophrenia |
| flupenthixol | Schizophrenia |
| iloperidone | Schizophrenia |
| loxapine | Schizophrenia |
| mesoridazine | Schizophrenia |
| promazine | Schizophrenia |
| reserpine | Schizophrenia |
| thioridazein | Schizophrenia |
| zuclopenthixol | Schizophrenia |
| asenapine | Schizophrenia & Bipolar disorder |
| levomepromazine | Schizophrenia & Bipolar disorder |
| ziprasidone | Schizophrenia & Bipolar disorder |
| molindone | Schizophrenia & Psychosis |
| pimozide | Schizophrenia & Psychosis |
| thioridazine | Schizophrenia & Psychosis |
| Cytarabine | Chemotherapy, hematological malignancies |

According to some embodiments, the surgical cannula is used to remove or withdraw a substance therethrough from the target area. According to some embodiments, the surgical cannula is used to remove cerebral spinal fluid from the patient.

Embodiments of the present invention may include steps, features, aspects, components, procedures and/or systems as disclosed in U.S. patent application Ser. No. 12/236,854, published as U.S. Published Patent Application No. 2009/0071184, the disclosure of which is incorporated herein by reference.

According to some embodiments, the systems are configured to provide a substantially automated or semi-automated and relatively easy-to-use MRI-guided system with defined workflow steps and interactive visualizations. In particular embodiments, the systems define and present workflow with discrete steps for finding target and entry point(s), guiding the alignment of the targeting cannula to a planned trajectory, monitoring the insertion of the delivery cannula, and adjusting the (X-Y) position in cases where the placement needs to be corrected. During steps where specific MR scans are used, the circuit or computer module can display data for scan plane center and angulation to be entered at the console. The workstation/circuit can passively or actively communicate with the MR scanner. The system can also be configured to use functional patient data (e.g., fiber tracks, fMRI and the like) to help plan or refine a target surgical site and/or access path.

Embodiments of the present invention will now be described in further detail below with reference to the figures. FIG. 1 illustrates an MRI-guided interventional system 10 with an MRI scanner 20, a clinician workstation 30 with at least one circuit 30c, at least one display 32, an MRI compatible trajectory guide 50t, a depth stop 70 (FIG. 5), and a fluid substance delivery system 80. The fluid substance delivery system includes an MRI-compatible intrabody surgical or delivery cannula 100, an infusion pump 82 and connecting tubing 84. The system 10 can be configured to render or generate real time visualizations of the target anatomical space using MRI image data and predefined data of at least one surgical tool to segment the image data and place the trajectory guide 50t and the cannula 100 in the rendered visualization in the correct orientation and position in 3D space, anatomically registered to a patient. The trajectory guide 50t and the cannula 100 can include or cooperate with tracking, monitoring and/or interventional components.

The tools of the system 10, including the cannula 100, can be provided as a sterile kit (typically as single-use disposable hardware) or in other groups or sub-groups or even individually, typically provided in suitable sterile packaging. The tools can also include a marking grid (e.g., as disclosed in U.S. Published Patent Application No. 2009-00177077 and/or U.S. Published Patent Application No. 2009/00171184). Certain components of the kit may be replaced or omitted depending on the desired procedure. Certain components can be provided in duplicate for bilateral procedures.

Figure 5:
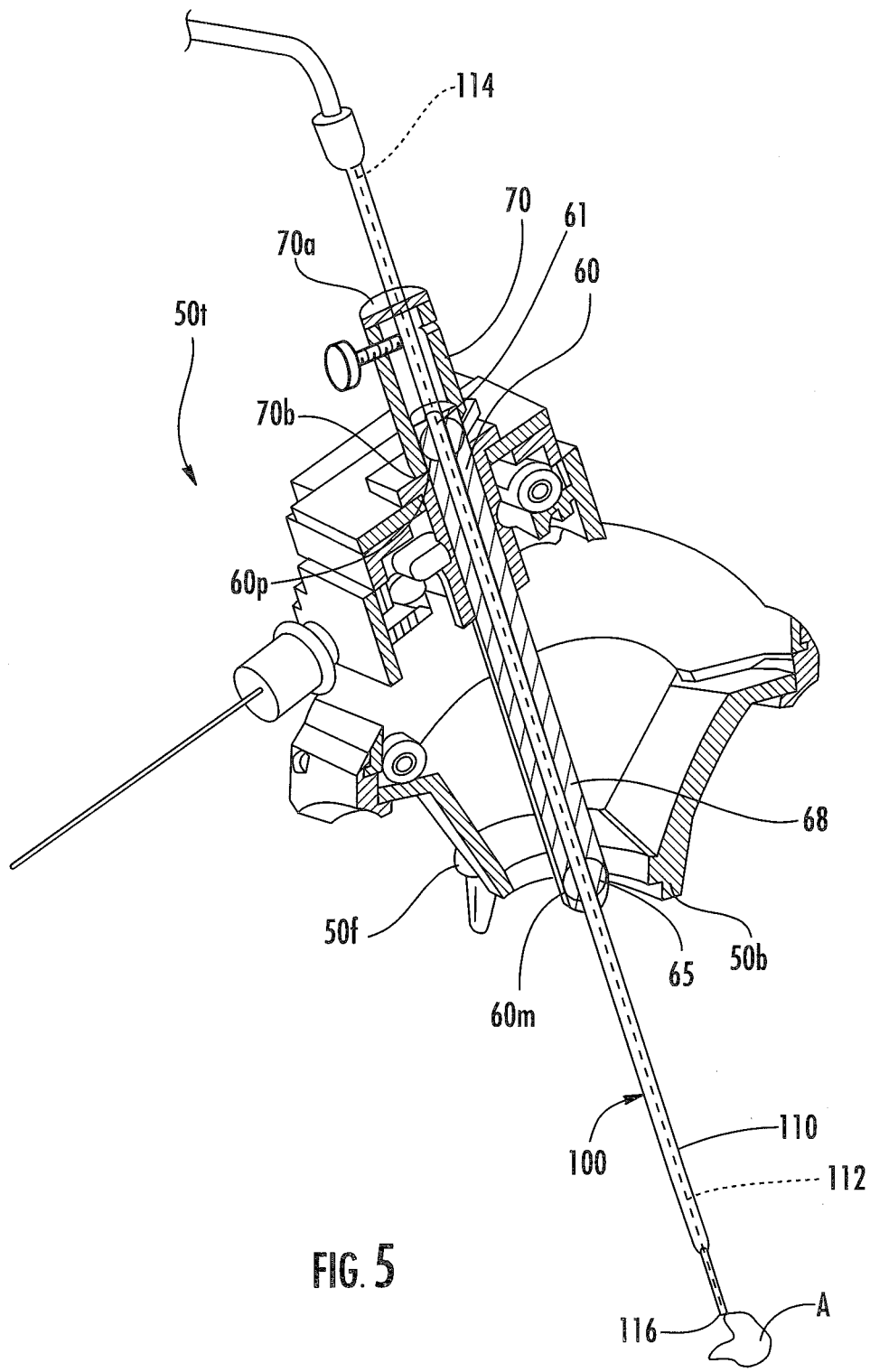
FIG. 5 is a sectional view of the trajectory guide of FIG. 2 with a surgical cannula forming a part of the MRI-guided surgical system according to embodiments of the present invention.

With reference to FIG. 5, the depth stop 70 has a generally cylindrical configuration with opposite proximal and distal ends 70a, 70b and is adapted to be removably secured within the proximal end of the tubular trajectory guide member 50t. The depth stop 70 can be attached to the cannula 100 to allow for a defined insertion depth where insertion depth control and/or locking, is desired.

The cannula 100 can be configured to flowably introduce and/or inject a desired therapy (e.g., antigen, gene therapy, chemotherapy or stem-cell or other therapy type). The cannula 100 as shown in FIG. 5 includes a cannula body 110 defining at least one longitudinally extending lumen 112, an inlet port 114 and at least one exit port 116. The cannula 100 is formed of an MRI-compatible, MRI-visible material such as ceramic. The cannula 100 as depicted in FIG. 5 is a relatively simple embodiment and further embodiments including additional functionality will be disclosed hereinbelow with reference to FIGS. 8-12E. These further embodiments of cannula may be used in the same manner as described with regard to the cannula 100.

The lumen 112 is fluidly connected to the pump 82 by the tubing 84. The tubing 84 may be flexible tubing. According to some embodiments, the tubing 84 is PVC tubing. According to some embodiments, the tubing 84 is silicone tubing.

Figure 3:
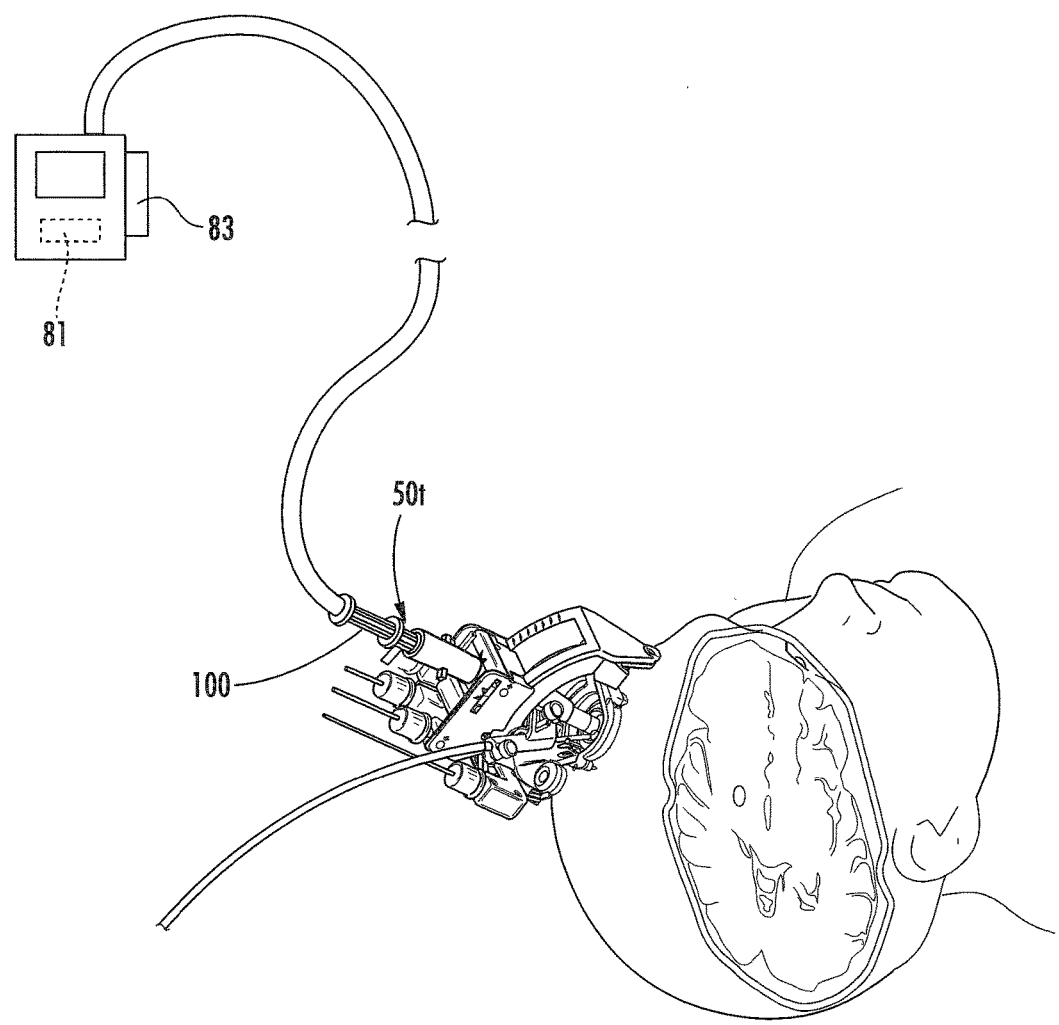
FIG. 3 is a side perspective view of a part of the MRI-guided surgical system of FIG. 1 mounted on the patient.

According to some embodiments and with reference to FIG. 3, the pump 82 includes a reservoir 83 of the substance to be delivered and a pump mechanism 81. The pump mechanism 81 is selectively operable to supply the substance to the lumen 112 under a controlled pressure. According to some embodiments, a syringe (e.g., a hand syringe) is used in place of the pump 82.

Figure 2:
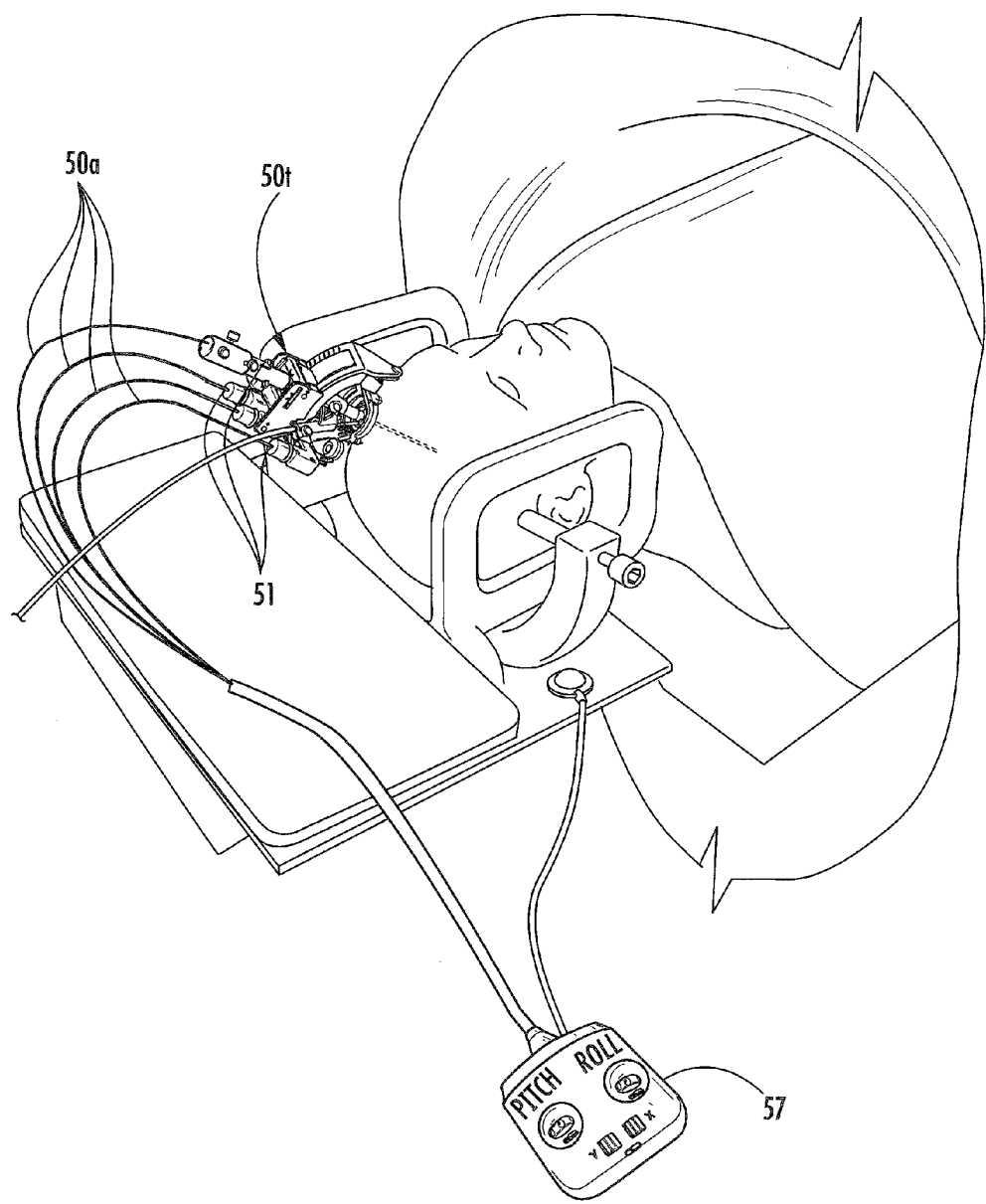
FIG. 2 is a side perspective view of a trajectory guide forming a part of the MRI-guided surgical system of FIG. 1 mounted on a patient.
Figure 4:
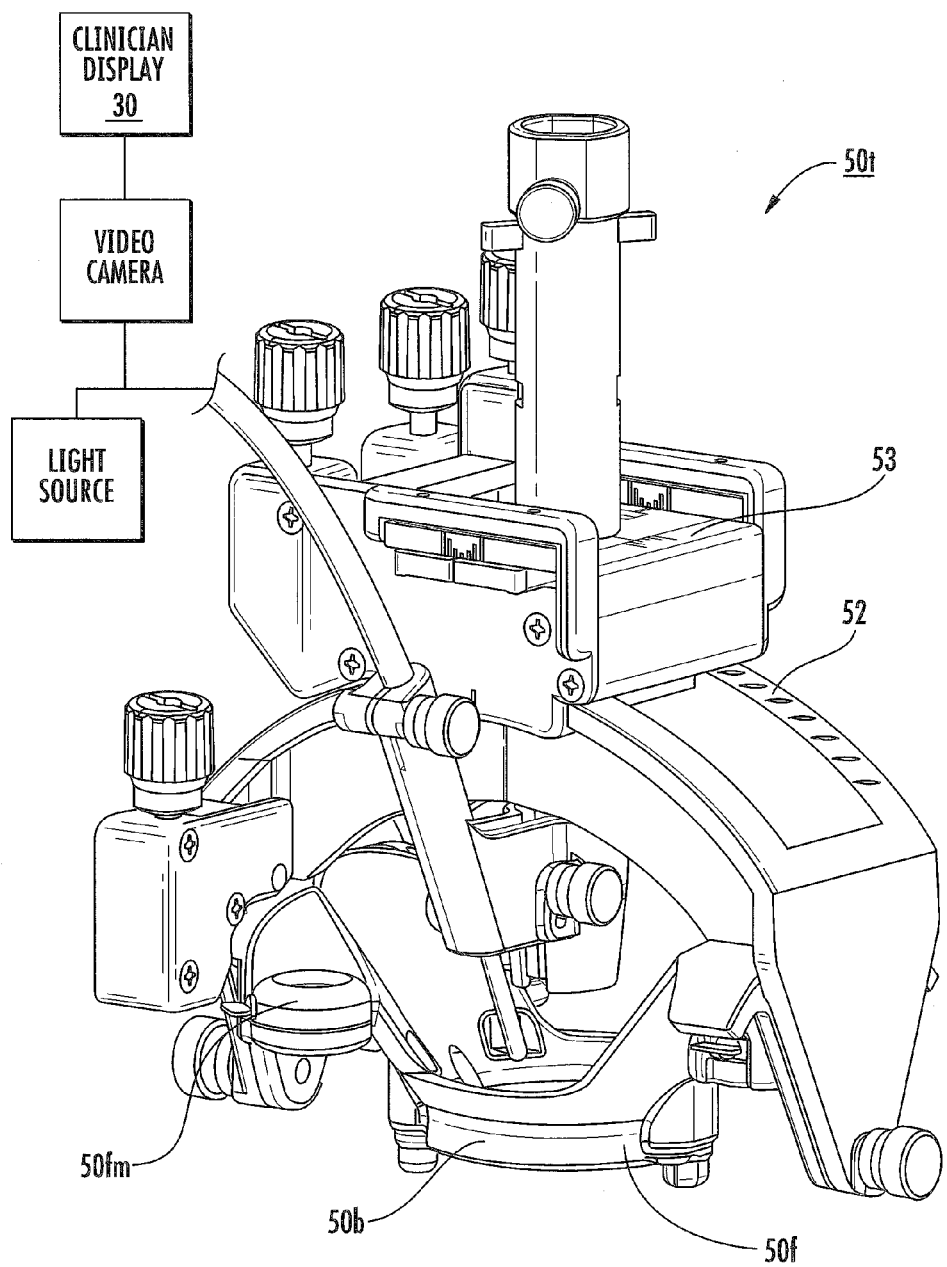
FIG. 4 is an enlarged, perspective view of the trajectory guide of FIG. 2.

An exemplary trajectory guide 50t is illustrated in FIGS. 1-3 in position on a patient. As shown, the trajectory guide 50t (FIG. 4) includes a guide frame 501, a targeting cannula 60 and trajectory guide actuators 51 having respective actuator cables 50a (FIG. 2) (providing X-Y adjustment and pitch and roll adjustment) in communication with a trajectory adjustment controller 57. The frame 50f can include a control arc 52 that cooperates with a platform 53 to provide pitch and roll adjustments. The platform 53 can allow for X-Y adjustments of the trajectory. The trajectory guide 50t may include a plurality of MRI-visible frame fiducial markers 50fm around a base 50b thereof. For additional discussion of suitable trajectory guides, see, U.S. Published Patent Application No. 2009-0112084, the contents of which are hereby incorporated by reference as if recited in full herein.

As shown in FIG. 5, the targeting cannula 60 includes an open center lumen or through passage 61 along the axis of the targeting cannula 60. The distal end portion of the targeting cannula 60 can include a fiducial marker 60m (typically including a fluid-filled component 65), shown as a substantially spherical or round (cross-section) marker shape. The proximal end 60p can be configured with a fluid filled channel 68 concentric with the passage 61 that can define a cylindrical fiducial marker. Other fiducial marker types can be used. The cannula 100 can be slidably introduced and/or withdrawn through the lumen or passage 61.

An MRI scanner interface 40 (FIG. 1) may be used to allow communication between the workstation 30 and the scanner 20. The interface 40 and/or circuit 30c may be hardware, software or a combination of same. The interface 40 and/or circuit 30c may reside partially or totally in the scanner 20, partially or totally in the workstation 30, or partially or totally in a discrete device therebetween.

The MRI scanner 20 can include a console that has a "launch" application or portal for allowing communication to the circuit 30c of the workstation 30. The scanner console can acquire volumetric T1-weighted (post-contrast scan) data or other image data (e.g., high resolution image data for a specific volume) of a patient's head or other anatomy. In some embodiments, the console can push DICOM images or other suitable image data to the workstation 30 and/or circuit 30c. The workstation 30 and/or circuit 30c can be configured to passively wait for data to be sent from the MR scanner 20 and the circuit 30c/workstation 30 does not query the scanner or initiate a communication to the scanner. In other embodiments, a dynamic or active communication protocol between the circuit 30c/workstation 30 and the scanner 20 may be used to acquire image data and initiate or request particular scans and/or scan volumes. Also, in some embodiments, pre-DICOM, but reconstructed image data, can be sent to the circuit 30c/workstation 30 for processing or display. In other embodiments, pre-reconstruction image data (e.g., substantially "raw" image data) can be sent to the circuit 30c/workstation 30 for Fourier Transform and reconstruction.

Generally described, for some unilateral scenarios, the user (e.g., doctor or surgeon) will proceed through a set of discrete workflow steps to load MR image data, identify a target point, identify an entry point, verify the planned trajectory, and align the targeting cannula 60. A target point or region can also be planned or refined based on real-time functional image data of a patient. The functional image data can include, but is not limited to, images of fiber tracks, images of activity in brain regions during vocalization (e.g., reading, singing, talking), or based on physical or olfactory or sense-based stimulation, such as exposure to electrical (discomfort/shock input), heat and/or cold, light or dark, visual images, pictures or movies, chemicals, scents, taste, and sounds or the like) and/or using fMRI or other imaging techniques. The enhanced visualization may give neurosurgeons a much clearer picture of the spatial relationship of a patient's brain structures. The visualizations can serve as a trajectory guide for delivering a substance to the body (e.g., to the brain) via the surgical (intrabody) delivery cannula 100. In some embodiments, the visualizations can be generated using data collated from different types of brain-imaging methods, including conventional magnetic resonance imaging (MRI), functional MRI (fMRI), diffusion-tensor imaging (DTI) and even hyperpolarized noble gas MRI imaging. The MRI gives details on the anatomy, fMRI or other active stimulation-based imaging protocol can provide information on the activated areas of the brain, and DTI provides images of the network of nerve fibers connecting different brain areas. The fusion of one or all of these different images and the tool information can be used to produce a 3-D display with trajectory information that surgeons can manipulate.

Thus, a target location and trajectory can be planned, confirmed or refined based in-part on functional information of the patient. This functional information can be provided, in a user interface (UI) displayed on the display screen 32, in near real-time visualizations of the patient with the trajectory guide tools for trajectory path and target planning, e.g., visualize a patient's fiber track structures and/or functional information of a patient's brain for a surgeon's ease of reference. Knowing where susceptible or sensitive brain regions are or where critical fiber tracks are in the patient's brain, can allow a surgeon to plan a better or less-intrusive trajectory and/or allow a surgeon to more precisely reach a desired target site and/or more precisely place a device and/or deliver a planned therapy substance.

To align the targeting cannula 60, scan volumes can be defined by the system based on known dimensions of the cannula, such as a cannula length a position of a proximal or distal marker on the cannula, and angulation and lateral (X-Y) pivot limit.

An estimated distance from the distal tip of the cannula 100 to a reference point on the guide frame 50t (FIGS. 2 and 3) or the targeting cannula 60 (e.g., the proximal end of the targeting cannula 60) can be determined and physically or visually marked on the cannula 100. The depth stop 70 can be secured about the cannula 100 at the marked location. The depth stop 70 can serve to limit the depth of insertion of the cannula 100 into the patient in a subsequent insertion step or steps.

The user can then (gradually) advance the cannula 100 and acquire images (on the display of the UI) to verify the trajectory and/or avoid functionally sensitive structure as appropriate. When the delivery cannula 100 has been advanced to the target point, high-resolution confirmation images can be obtained to verify the cannula tip location relative to the planned location. Additionally or alternatively, electrical activity can be sensed using an electrode at a tip of the cannula 100. If actual placement is not correct, the cannula 100 can be withdrawn. At that point, either the X-Y placement can be adjusted appropriately (e.g., by moving a platform or stage an amount to cause the desired adjustment) or a trajectory angulation can be re-planned and a second attempt can be made.

For some bilateral scenarios, the above steps can be repeated for both left and right sides, with the additional goal that the patient should not be moved into or out of the scanner. To satisfy that goal, trajectory planning should be completed for both sides prior to removing the patient from the scanner. Also, burring and frame attachment (the member that holds the trajectory guide to the patient's head) should be completed for both sides prior to moving the patient back into the scanner 20 to promote speed of the procedure.

The system 10 can be configured with a (hardware/software) interface that provides a network connection, e.g., a standard TCP/IP over Ethernet network connection, to provide access to MR scanner 20, such as the DICOM server. The workstation 30 can provide a DICOM C-STORE storage class provider. The scanner console can be configured to be able to push images to the workstation 30 and the workstation 30 can be configured to directly or indirectly receive DICOM MR image data pushed from an MR scanner console. Alternatively, as noted above, the system can be configured with an interface that allows for a dynamic and interactive communication with the scanner 20 and can obtain image data in other formats and stages (e.g., pre-DICOM reconstructed or raw image data).

As noted above, the system 10 is configured so that hardware, e.g., the trajectory guide 50t and/or the cannula 100, constitute a point of interface with the system (software or computer programs) because the circuit 30c is configured with predefined tool data that recognizes physical characteristics of specific tool hardware.

The system 10 may also include and implement a marking grid and/or non-uniformly spaced-apart frame fiducial markers as disclosed in U.S. patent application Ser. No. 12/236,854, published as U.S. Published Patent Application No. 2009/00171184.

In some embodiments, circuit 30c can be configured so that the program application can have distinct ordered workflow steps that are organized into logical groups based on major divisions in the clinical workflow as shown in Table 2. A user may return to previous workflow steps if desired. Subsequent workflow steps may be non-interactive if requisite steps have not been completed. The major workflow groups and steps can include the following features or steps in the general workflow steps of "start", "plan entry", "plan target", "navigate", and "refine," ultimately leading to delivering and visualizing the therapy (i.e., delivering the substance to the target through the cannula 100) as described in Table 2.

TABLE 2

Exemplary Clinical Workflow Groups/Steps

| Group | Step | Description |
|---|---|---|
| Start | Start | Set overall procedure parameters (Optionally confirm hardware compatibility) |
| Plan Entry | ACPC | Acquire a volume and determine AC, PC, and MSP points |
| | Target | Define initial target point(s) for entry planning |
| | Trajectory | Explore potential trajectories to determine entry point(s) |
| | Grid | Locate physical entry point via fiducial grid. |
| Plan Target | ACPC | With hole burred and frame attached, acquire a volume and determine revised AC, PC, and MSP points. |
| | Target | Acquire high-resolution slabs (e.g., T2 slabs) to determine target positions in new volume. |
| | Trajectory | Review final planned trajectory prior to starting procedure. |
| Navigate | Initiate | Acquire slabs to locate initial position of cannula. |
| | Alignment | Dynamically re-acquire scan showing position of top of cannula. With each update show projected target position to determine when alignment is correct. |

TABLE 2-continued

Exemplary Clinical Workflow Groups/Steps

| Group | Step | Description |
|---|---|---|
| | Insertion | Acquire slabs as cannula 100 is inserted into brain. Verify that cannula 100 is following planned trajectory. |
| Refine | Target | Acquire images with cannula 100 in place. Review position and redefine target if necessary. |
| | Adjust XY Offset | Dynamically re-acquire scan showing position of bottom of targeting cannula 60. With each update show projected target position to determine when offset is correct. |
| | Insertion | Acquire slabs as cannula 100 is inserted into brain. Verify that cannula 100 is following planned trajectory. |
| Delivery or Withdrawal | Substance Delivery | Once cannula 100 position is finalized, prompt user to begin delivery or withdrawal of substance through cannula 100. |
| | Watch Diffusion Delivery Pattern | Acquire slabs as substance is delivered into or withdrawn from brain and display. |
| Admin | Admin | Reporting and Archive functionality |

The AC, PC and MSP locations can be identified in any suitable manner. In some embodiments, the AC-PC step can have an automatic, electronic AC, PC MSP Identification Library. The AC, PC and MSP anatomical landmarks define an AC-PC coordinate system, e.g., a Talairach-Tournoux coordination system that can be useful for surgical planning. This library can be used to automatically identify the location of the landmarks. It can be provided as a dynamic linked library that a host application can interface through a set of Application Programming Interface (API) on Microsoft Windows®. This library can receive a stack of MR brain images and fully automatically locates the AC, PC and MSP. The success rate and accuracy can be optimized, and typically it takes a few seconds for the processing. The output is returned as 3D coordinates for AC and PC, and a third point that defines the MSP. This library is purely computation and is typically UI-less. This library can fit a known brain atlas to the MR brain dataset. The utility can be available in form of a dynamic linked library that a host application can interface through a set of Application Programming Interface (API) on Microsoft Windows®. The input to this library can contain the MR brain dataset and can communicate with applications or other servers that include a brain atlas or include a brain atlas (e.g., have an integrated brain atlas). The design can be independent of any particular atlas; but one suitable atlas is the Cerefy® atlas of brain anatomy (note: typically not included in the library). The library can be configured to perform segmentation of the brain and identify certain landmarks. The atlas can then be fitted in 3D to the dataset based on piecewise affine transformation. The output can be a list of vertices of the interested structures.

In some embodiments, the mid-sagittal plane (MSP) is approximated using several extracted axial slices from the lower part of the input volume, e.g., about 15 equally spaced slices. A brightness equalization can be applied to each slice and an edge mask from each slice can be created using a Canny algorithm. A symmetry axis can be found for each edge mask and identify the actual symmetry axis based on an iterative review and ranking or scoring of tentative symmetry axes. The ranking/scoring cam can be based on whether a point on the Canny mask, reflected through the symmetry axis lands on the Canny mask (if so, this axes is scored for that slice). An active appearance model (AAM) can be applied to a brain stem in a reformatted input stack with the defined MSP to identify the AC and PC points.

The MSP plane estimate can be refined as well as the AC and PC points. The MSP plane estimate can be refined using a cropped image with a small region that surrounds a portion of the brain ventricle and an edge mask using a Canny algorithm. The symmetry axis on this edge mask if found following the procedure described above. The AC and PC points are estimated as noted above using the refined MSP and brightness peaks in a small region (e.g., 6×6 mm) around the estimate are searched. The largest peak is the AC point. The PC point can be refined using the PC estimate above and the refined MSP. A Canny edge map of the MSP image can be computed. Again, a small region (e.g., about 6 mm×6 mm) can be searched for a point that lies on a Canny edge and for which the image gradient is most nearly parallel to the AC-PC direction. The point is moved about 1 mm along the AC-PC direction, towards PC. The largest intensity peak in the direction perpendicular to AC-PC is taken to be the PC point.

It will be appreciated that when the target is a tumor or ventricle to be infused or the like, the AC-PC points typically will not be used to provide guidance.

The Navigation-Insertion step may include further aspects as described in Table 3A:

TABLE 3A

Navigate - Insertion
Description

The application can provide a depth value to set on the cannula 100 prior to insertion.
The application can prompt with scan parameters for oblique coronal and sagittal planes aligned to the trajectory. Also for an oblique axial perpendicular to the trajectory.
On receiving coronal or sagittal images, the application can display an overlay graphic indicating the planned trajectory. The most recent coronal and sagittal images can appear together in a 1 × 2 display.
On receiving a trajectory axial scan perpendicular to the trajectory, the application can segment out the cross-sections of the cannula 100 to determine the actual path being followed by the cannula 100.
On receiving a trajectory axial scan perpendicular to the trajectory, the application can display two viewports containing:
the axial stack with graphic overlays showing the detected path of the cannula 100 on each image
an anatomic axial view through the target showing the planned target and the target projected from the detected path of the cannula 100. An error value can show the distance between the current projected target and the planned target.
If multiple trajectories have been defined for a single entry, the application can display the trajectory that is currently aligned during insertion.

The application may provide a depth value that is the expected distance from the target to the top of the targeting cannula 60. The operator can measure the depth value distance from the distal tip of the cannula 100 and mark the proximal end point on the cannula 100 (e.g., with a sterile marker). The depth stop 70 can then be secured at the marked location and the measured insertion distance verified. The depth stop 70 is configured to limit a distance that the cannula 100 extends into the body of a patient when the depth stop is inserted within the targeting cannula 60, so that full insertion of the cannula 100 up to the depth stop will provide the desired insertion depth.

In the event that the placement is not acceptable, the user may opt to proceed to the X-Y Adjustment workflow step as described in Table 3B:

TABLE 3B

Refine-Adjust X-Y Offset

Description

The X-Y Adjustment step can display the current target and projected point as annotations to the image data that was acquired during the Target Refinement step.
This step can prompt the user to acquire 2D images with scan plane parameters such that the image lies perpendicular to the trajectory and through the pivot point.
On receiving a 2D image through the pivot point, the step can calculate the current projected target.
This step can display lines from the current projected target to the revised target that indicate the track the projected target would travel if the X and Y offset wheels were turned independently. The lines can be colored to match colors on the control wheels for X and Y offset respectively. A tool-tip (e.g., pop-up) can provide text to describe the necessary action. (For example: "Turn X-offset knob to the Left")
This step can display an annotation indicating the location of the original planned target.
When drawing the target and the current projection of the cannula path, the annotations can be drawn to match the physical size of the cannula 100 diameter.

After the cannula 100 has been placed and the position has been accepted by the user, the user may proceed to the substance delivery or withdrawal step.

Again, it is noted that functional patient data can be obtained in near real-time and provided to the circuit 30c/workstation 30 on the display 32 with the visualizations of the patient anatomy to help in refining or planning a trajectory and/or target location for placement of the cannula 100.

The system 10 can provide a UI to set target points so that the trajectories through potential entry points can be investigated. The user may opt to overlay the outlines from a standard brain atlas over the patient anatomy for comparison purposes which may be provided in color with different colors for different structures. When using the brain atlas, the user may opt to show either just the target structure (STN or GPi) or all structures. In either case, a tooltip (e.g., pop-up) can help the user to identify unfamiliar structures. The user may also opt to scale and/or shift the brain atlas relative to the patient image to make a better match. To do this, the user may drag the white outline surrounding the brain atlas template. Fiber track structures and/or functional information of a patient's brain can be provided in a visually prominent manner (e.g., color coded or other visual presentation) for a surgeon's ease of reference.

The UI can display images and information that enable the user to see how well the cannula 100 is following the planned trajectory. The user may opt to scan Axial, Coronal and Sagittal slabs along the cannula 100 to visually determine the cannula 100 alignment in those planes. The user can also scan perpendicular to the cannula 100. In that case, the circuit 30c (e.g., software) can automatically identify where the cannula 100 is in the slab and it then shows a projection of the current path onto the target plane to indicate the degree and direction of error if the current path is continued. The user can perform these scans multiple times during the insertion. The automatic segmentation of the cannula 100 and the display of the projected target on the target plane provide fully-automatic support for verifying the current path. The Coronal/Sagittal views can provide the physician with a visual confirmation of the cannula 100 path that does not depend on software segmentation.

After completing the initial insertion of the cannula 100, the user (e.g., physician) may find that either the placement does not correspond sufficiently close or perfectly to the plan, or the plan was not correct. The UI can support functionality whereby the physician can withdraw the cannula 100 and use the X and Y offset adjustments to obtain a parallel trajectory to a revised target. The UI can prompt the user or otherwise acquire an image slab through the distal tip of the cannula 100. The UI can display the slab and on it the user may opt to modify the target point to a new location or accept the current position as final.

The UI can also support the user in adjusting a small X-Y offset to set the targeting cannula 60 to a trajectory parallel to the original one. The UI can provide visualization of the position of the cannula 100 tip relative to the target and with instructions on what physical adjustments to make to obtain the desired parallel trajectory (shown as "turn Y wheel to the right") and the projected error.

After the angular and/or X-Y adjustments are made, the cannula 100 insertion is carried out in the same manner as described above.

After the cannula 100 has been inserted and had its position verified by the physician, the UI can prompt the physician to begin delivery of the substance to the target via the cannula 100. In some embodiments, a test spray of a biocompatible fluid of similar density to the target therapeutic substance (e.g., saline) may be first delivered to the target.

The physician (or other operator) then actuates the pump (or syringe) 82 to begin driving a flow of the therapeutic substance through the tubing 84 and the lumen 112 of the cannula 100. A mass flow of the substance exits the cannula 100 through the exit port 116 into the target region T or the vicinity of the target region T.

Using MRI image data, the system 10 may render or generate near real time visualizations of the infused or delivered substance along with the near real time visualizations of the target anatomical space and the cannula 100 in the UI. That is, in the same or similar manner to the segmentation and visualization/display of the patient anatomy, the application can segment out the cross-sections of the delivered substance to determine the actual volume occupied by the delivered substance. Scans of scan planes proximate the distal tip of the cannula 100 or associated with target regions can be acquired. The MR image data can be obtained and the actual distribution of the delivered substance in tissue can be shown on the display. These visualizations can be dynamically rendered (e.g., in near real time) to show the dynamic dispersion and/or infusion pattern and/or path of the infused substance. In some embodiments, an MR contrast agent or fluid can be provided in the delivered substance having an increased SNR relative to the tissue.

Figure 6A:
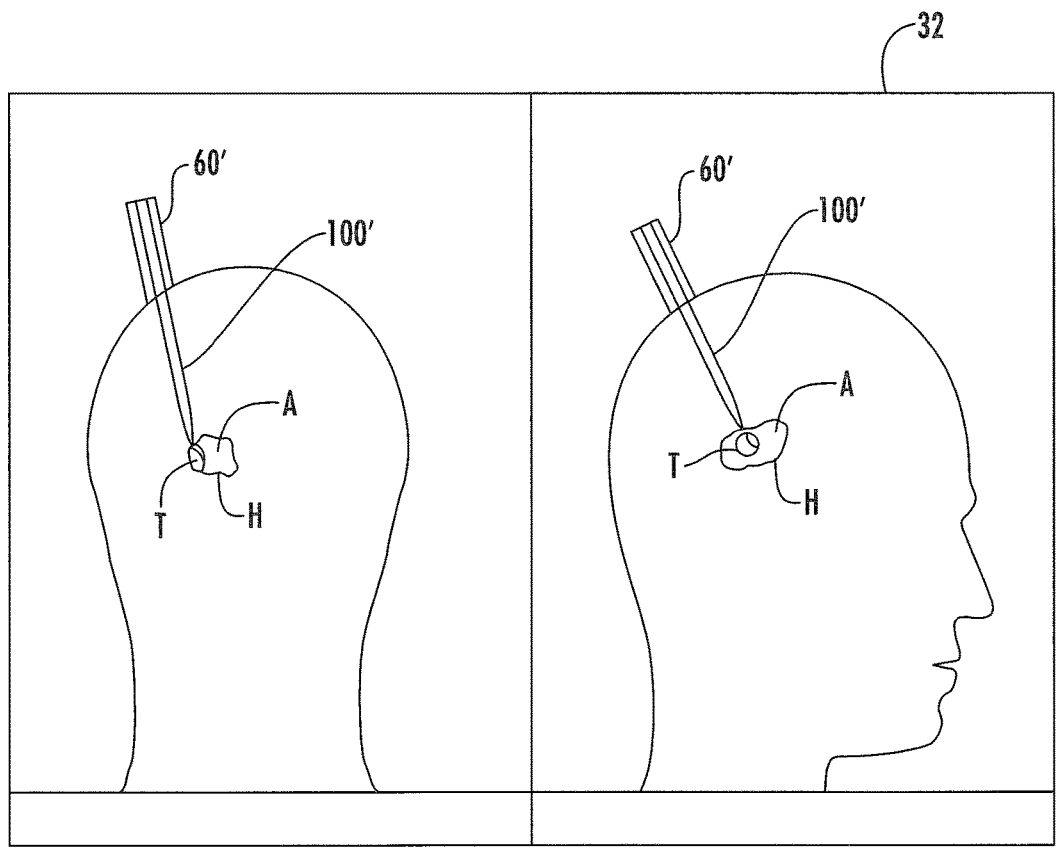
FIGS. 6A-6C and 7A-7B are schematic illustrations of exemplary screen shots of displays of a User Interface provided to a user to facilitate navigation and/or assessment steps of an MRI-guided infusion procedure.
Figure 6B:
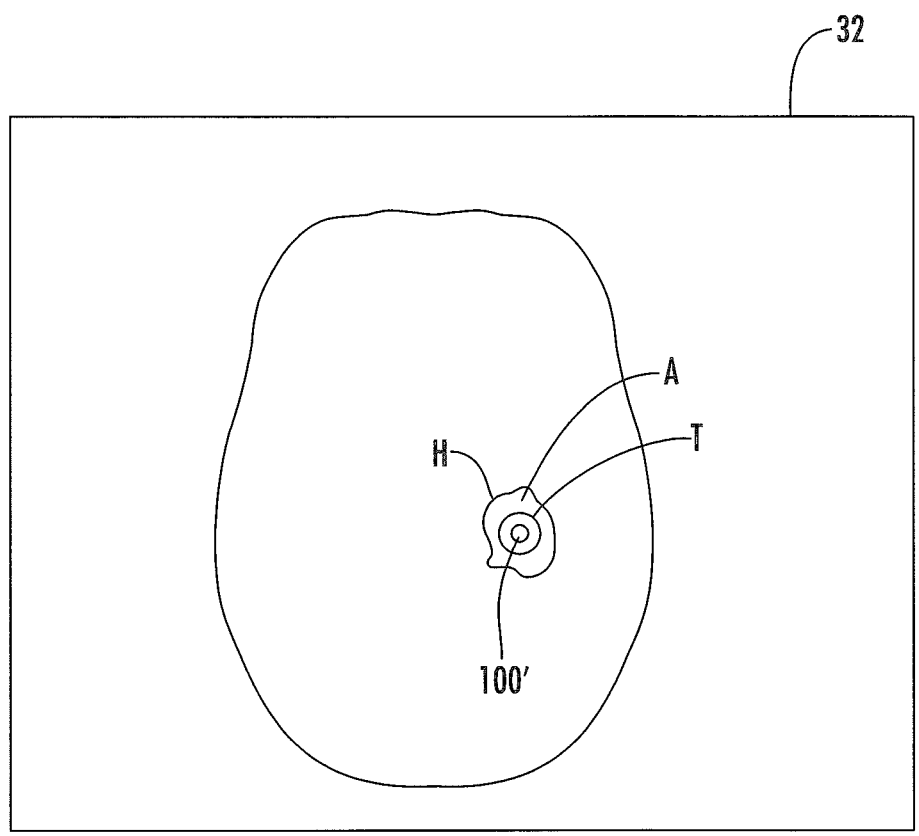

FIG. 6A illustrates a screen shot from the UI that allows the user to see the distribution of the delivered substance, which is represented in the UI by the displayed image A. This screen shot illustrates coronal and sagittal views to the target (e.g., STN). The user may opt to scan Coronal and Sagittal slabs along the cannula 100 to visually determine the distribution pattern or flow paths in those planes. The user can also scan perpendicular to the cannula 100. The cannula 100 is represented in the screen shot by an image 100' and the targeting cannula 60 is represented in the screen shot by an image 60'. FIG. 6B illustrates an axial slab through the target T. The user can perform these scans multiple times during delivery of the substance. The automatic segmentation and display of the delivered substance, the patient anatomy and the cannula 100 provide fully-automatic support for verifying or assessing the anatomical flow paths, diffusion, dispersion, permeation and/or other distribution of the delivered substance in the patient.

The delivered substance may be visually highlighted in the display of the UI. For example, a graphical overlay or outline H may be provided in one or more of the displayed views that highlights the image of the delivered substance A. By way of further example, the image of the delivered substance A in the tissue may be provided with a contrasting coloring or shading.

Figure 6C:
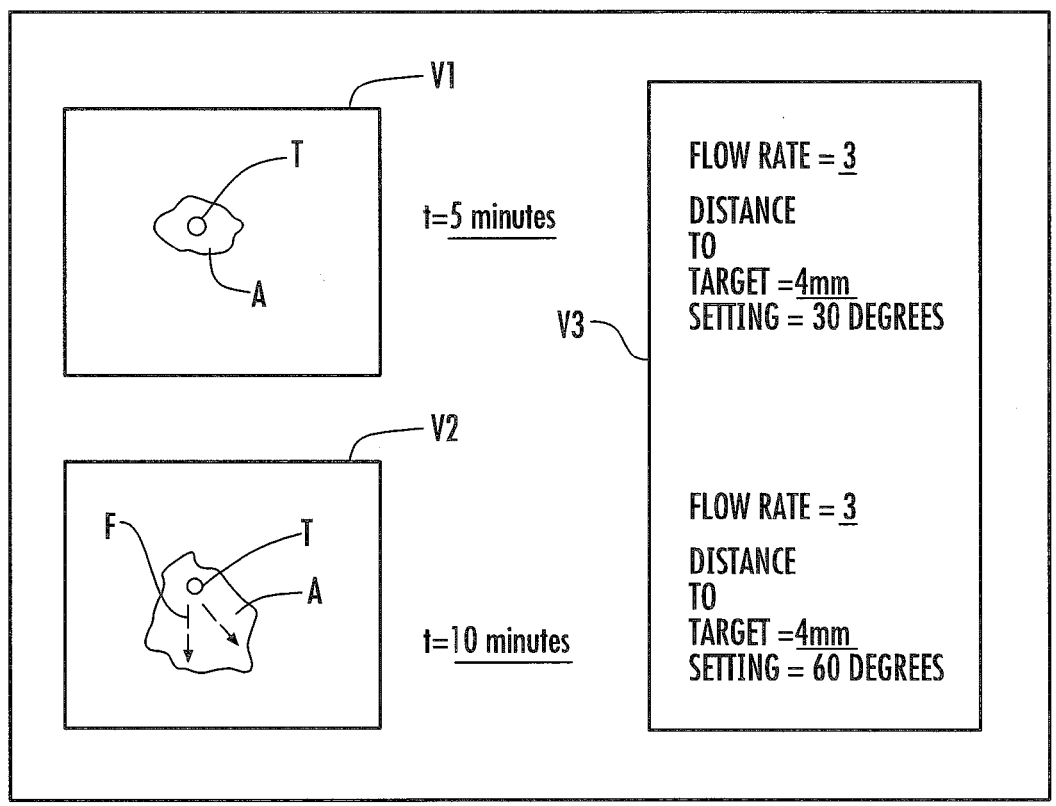

As noted above, the operator can perform scans multiple times during the procedure to track or assess the delivery performance. The UI may allow the operator to display the MR image data in a manner that assists the operator in comparing the flow and/or distribution of the delivered substance over time. FIG. 6C illustrates a screen shot from the UI including a view V1 including an image A of the delivered substance at a first time (e.g., "t=5 minutes") and a view V2 including an image A of the delivered substance A at a second, subsequent time (e.g., "t=10 minutes"). The UI may also display (e.g., in a view V3) relevant data such as the pump settings, flow rate, delivery cannula port settings, and/or nozzle angle at each of the selected times or any intervening adjustments. The UI may also display indicia F, such as graphical arrows indicating the directions of flow or dispersion, for example, between the selected times or over time. The foregoing visualization aids may assist the operator in assessing the effect of adjustments in flow rates, delivery cannula placement, or delivery cannula settings, for example.

Figure 7A:
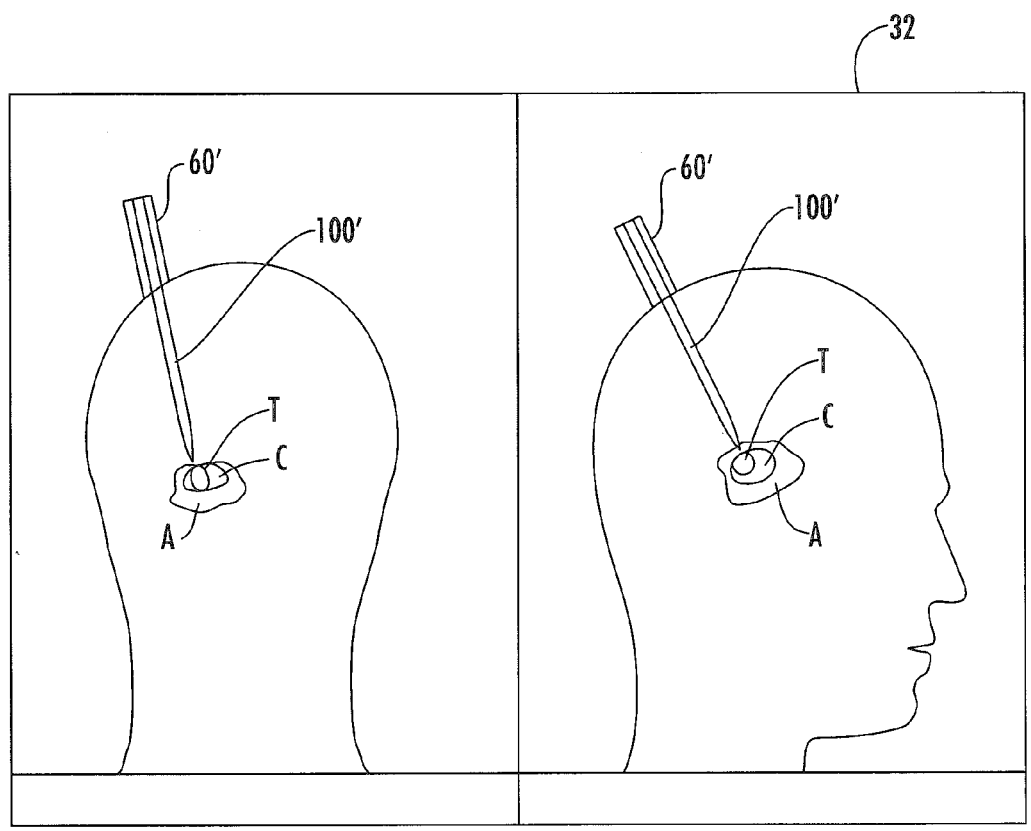
Figure 7B:
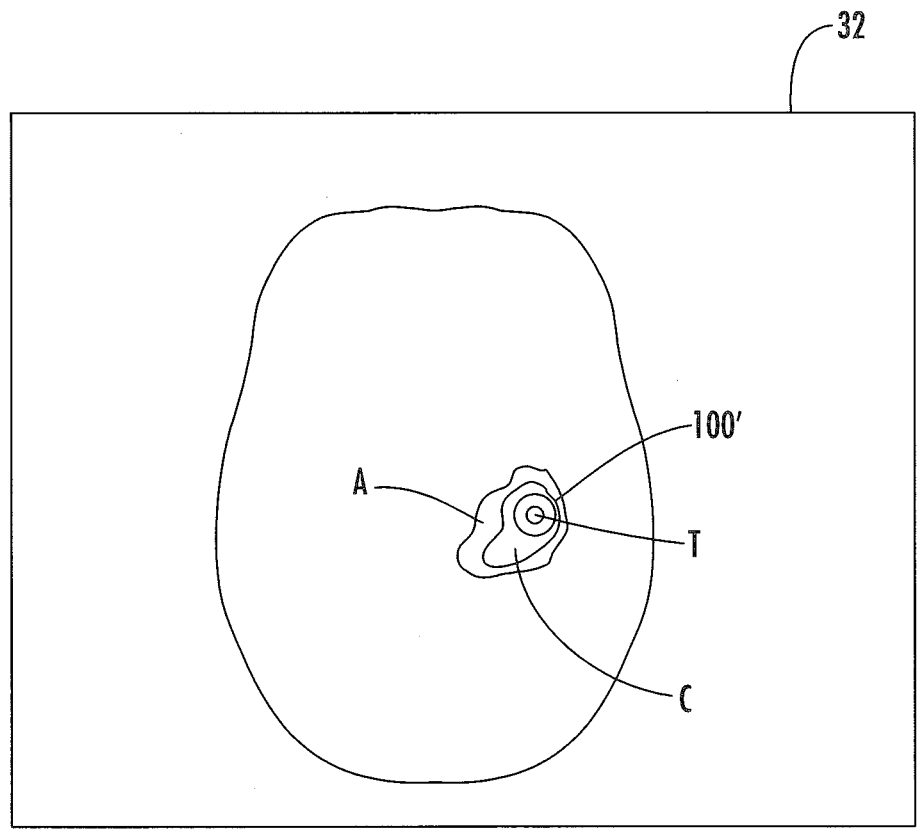

FIG. 7A illustrates a screen shot from the UI in the case where the target region is a tumor site in a patient's brain. The tumor site is segmented and displayed as a part of the patient anatomy and the image C of the tumor may be highlighted, enhanced, contrasted or otherwise augmented to enable the operator to more easily discern the tumor image C in the displayed image. The UI enables the user to see the distribution of the infused substance with respect to the tumor site. This screen shot illustrates coronal and sagittal views through the tumor. The user may opt to scan Coronal and Sagittal slabs along the cannula 100 to visually determine the distribution pattern or flow paths in those planes. The user can also scan perpendicular to the cannula 100. FIG. 7B illustrates an axial slab through the tumor. The user can perform these scans multiple times during delivery of the substance. The automatic segmentation and display of the infused substance, the patient anatomy (including the tumor) and the cannula 100 provide fully-automatic support for verifying or assessing the anatomical flow paths, diffusion, dispersion and distribution of the infused substance with respect to the tumor site and the remainder of the patient anatomy.

The operator can use the feedback from the UI to assess, re-plan and/or modify the infusion procedure.

Responsive to the UI feedback, the operator may adjust one or more operational parameters during the fluid delivery. For example, the mass flow rate of the substance exiting the cannula 100 can be increased or decreased. This may be accomplished by adjusting the mass flow rate setting of the infusion pump 82 or a regulator (e.g., restrictor or valve) upstream of the cannula 100. In some cases (e.g., as described below with reference to FIG. 10), the delivery cannula includes a flow control mechanism that can be used to adjust the mass flow rate of infusion.

The operator may adjust the placement of the exit port responsive to the UI feedback. For example, the operator may insert the cannula 100 further into the patient or withdraw the end of the cannula 100 somewhat from the patient. The operator may fully withdraw the cannula 100 from the patient, plan a new target and trajectory, re-insert the cannula 100 to the new target, and re-initiate delivery of the substance to the new target through the cannula 100. This procedure may be used one or more times in order to infuse the substance into different regions of a tumor, for example. Different cannulas or a protective (e.g., retractable) sheath may be used to inhibit spread of tumor cells.

The operator may adjust the delivery flow pattern of the substance exiting from the delivery cannula responsive to the UI feedback. This may be accomplished using a mechanism or mechanisms of a delivery cannula suitably modified to enable flow pattern modification. According to some embodiments (e.g., as described below with reference to FIGS. 9A-11), the cannula 200, 300, 400, 500 is configured to allow the operator to modify the delivery flow pattern in situ (i.e., while the delivery cannula is situated in the target region). The adjustment mechanism(s) may include a mechanism to adjust a size of an exit port, to adjust the number of open ports for substance egress, and/or to adjust (e.g., axially or circumferentially) the location of one or more open exit ports to adjust the nozzle angle and the like. These cannulae can have any other features described herein although not specifically discussed or shown.

Figure 8:
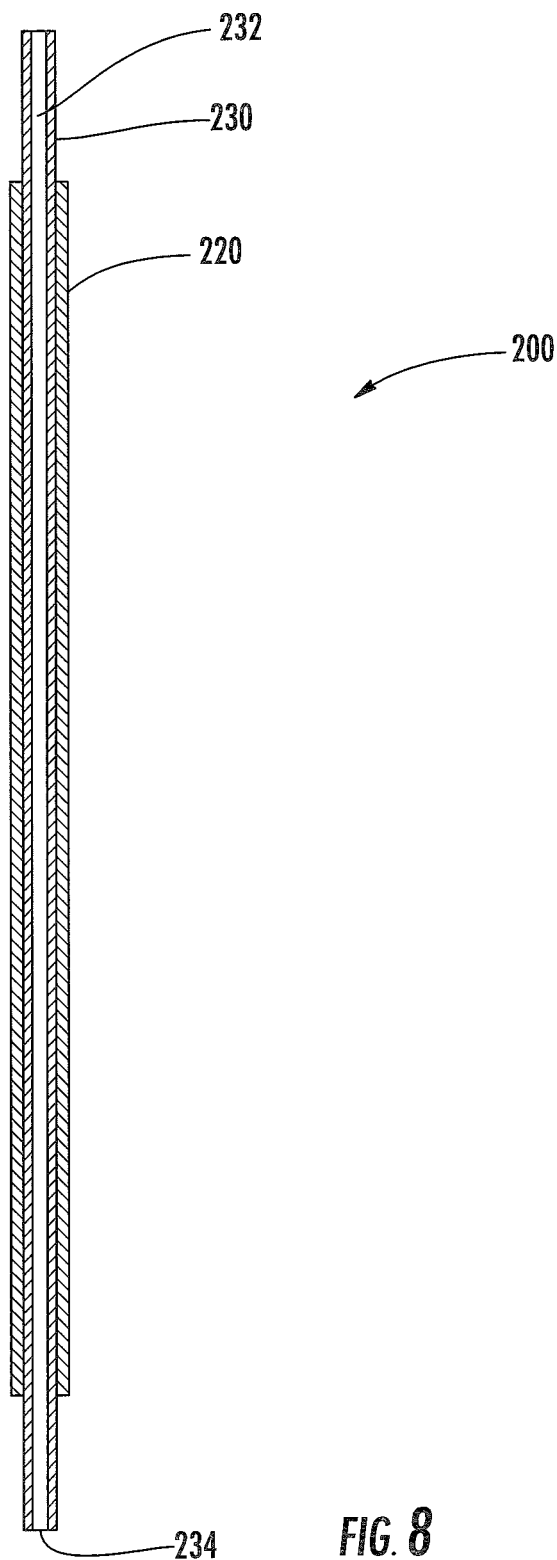
FIG. 8 is a cross-sectional view of a surgical cannula according to some embodiments of the present invention.

With reference to FIG. 8, one exemplary MRI-compatible intrabody surgical cannula (e.g., delivery cannula) 200 according to embodiments of the present invention is shown therein. It is noted that exemplary embodiments of the surgical cannula described herein can be used as described above with respect to the cannula 100. Also one or more features from one or more embodiments can be combined or used in other embodiments. The surgical cannula 200 includes a tubular outer sleeve 220 and a tubular inner sleeve 230 axially slidably mounted in the outer sleeve 220. The inner sleeve 230 defines a central lumen 232 and an exit port 234. In use, the inner sleeve 230 can be telescopingly extended and retracted relative to the outer sleeve 220 to selectively adjust the effective length of the surgical cannula 200 and the position of the exit port 234 with respect to the target region. The outer sleeve 220 can also act as a protective sheath that encases the inner sleeve 230 until the cannula tip reaches tissue proximate the tumor site, at which time the inner sleeve 230 can be extended. At withdrawal of the cannula 200, the inner sleeve 230 can be withdrawn or retracted into the outer sleeve 220 so as not to expose healthy tissue to tumor cells.

Figures 9A, 9B:
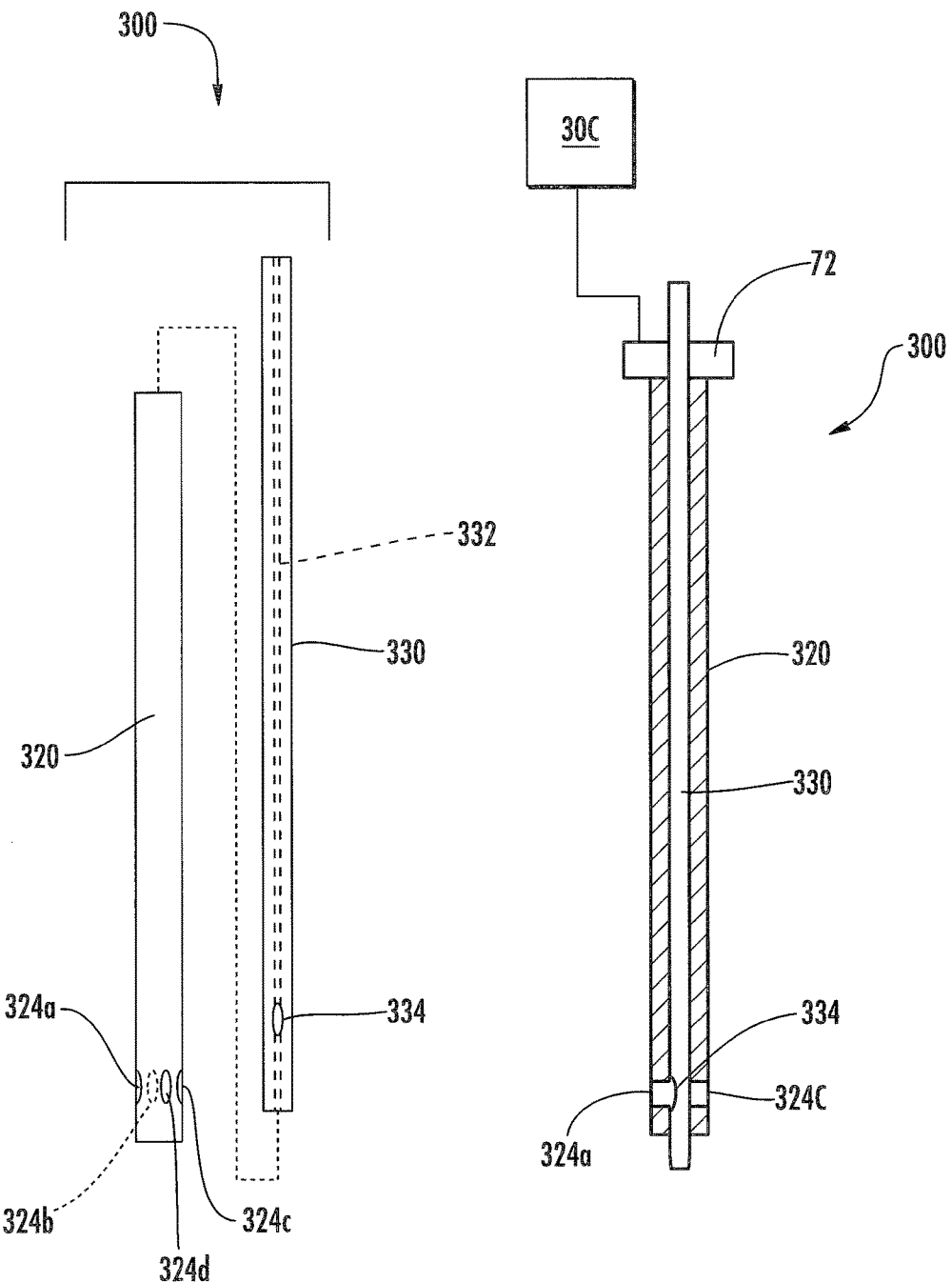
FIG. 9A is an exploded view of a surgical cannula according to further embodiments of the present invention.
FIG. 9B is a cross-sectional view of the assembled surgical cannula of FIG. 9A.

With reference to FIGS. 9A and 9B, an alternative MRI-compatible intrabody surgical cannula (e.g., delivery cannula) 300 according to embodiments of the present invention is shown therein and may be used in place of the cannula 100. The surgical cannula 300 includes a tubular outer sleeve 320 and a tubular inner sleeve 330 slidably mounted in the outer sleeve 320 to permit relative rotation between the sleeves 320, 330. The inner sleeve 330 defines a central lumen 332 and an exit port 334. The outer sleeve 320 defines four circumferentially spaced apart exit ports 324a, 324b, 324c, 324d. In use, the inner and outer sleeves 320, 330 can be relatively rotated to align the exit port 334, alternatively, with each of the exits ports 324a, 324b, 324c, 324d. In this way, the operator can selectively deliver the substance through a chosen side exit port 324a, 324b, 324c, 324d in each of four lateral directions. The side exit ports 324a, 324b, 324c, 324d can also be axially offset.

Figure 10:
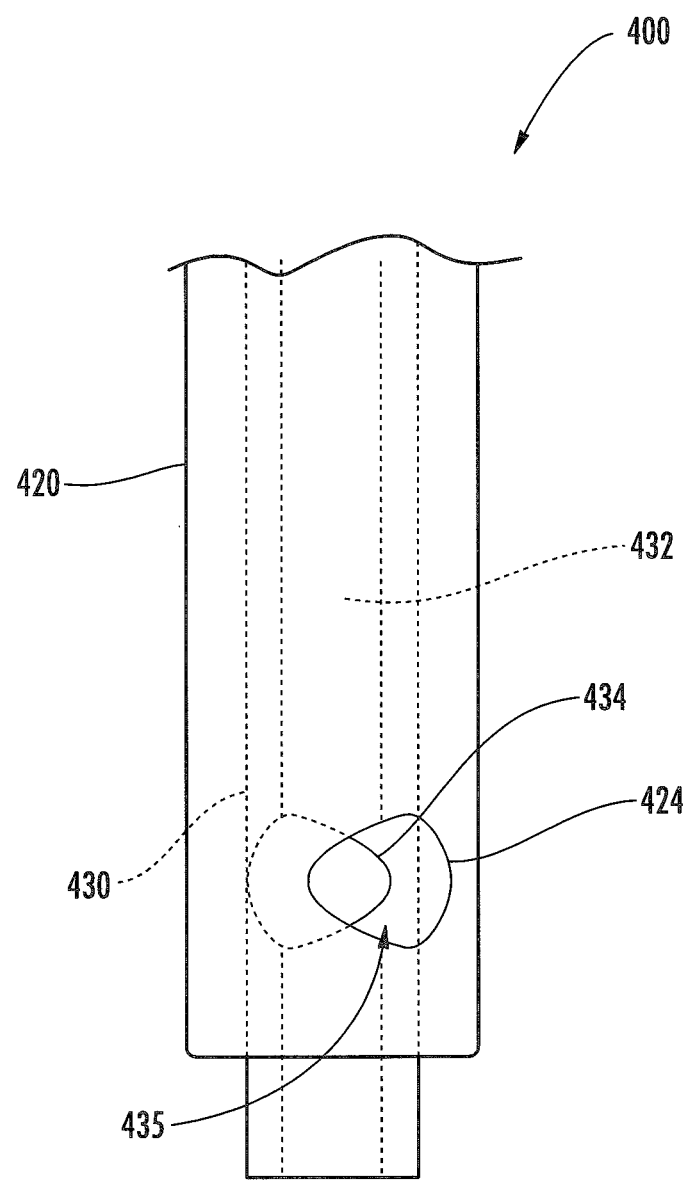
FIG. 10 is a fragmentary, side view of a surgical cannula according to further embodiments of the present invention.

With reference to FIG. 10, an alternative MRI-compatible intrabody surgical cannula (e.g., delivery cannula) 400 according to embodiments of the present invention is shown therein and may be used in place of the cannula 100. The surgical cannula 400 includes a tubular outer sleeve 420 and a tubular inner sleeve 430 slidably mounted in the outer sleeve 420 to permit relative rotation between the sleeves 420, 430. The inner sleeve 430 defines a central lumen 432 and an exit port 434. The outer sleeve 420 defines an exit port 424. In use, the inner and outer sleeves 420, 430 can be relatively rotated to align the exit ports 424, 434 with differing amounts of overlap. By selectively adjusting the overlap between the exit ports 424, 434, the size of the effective exit port 435, and thereby the mass flow rate of delivery, can be adjusted.

Figure 11:
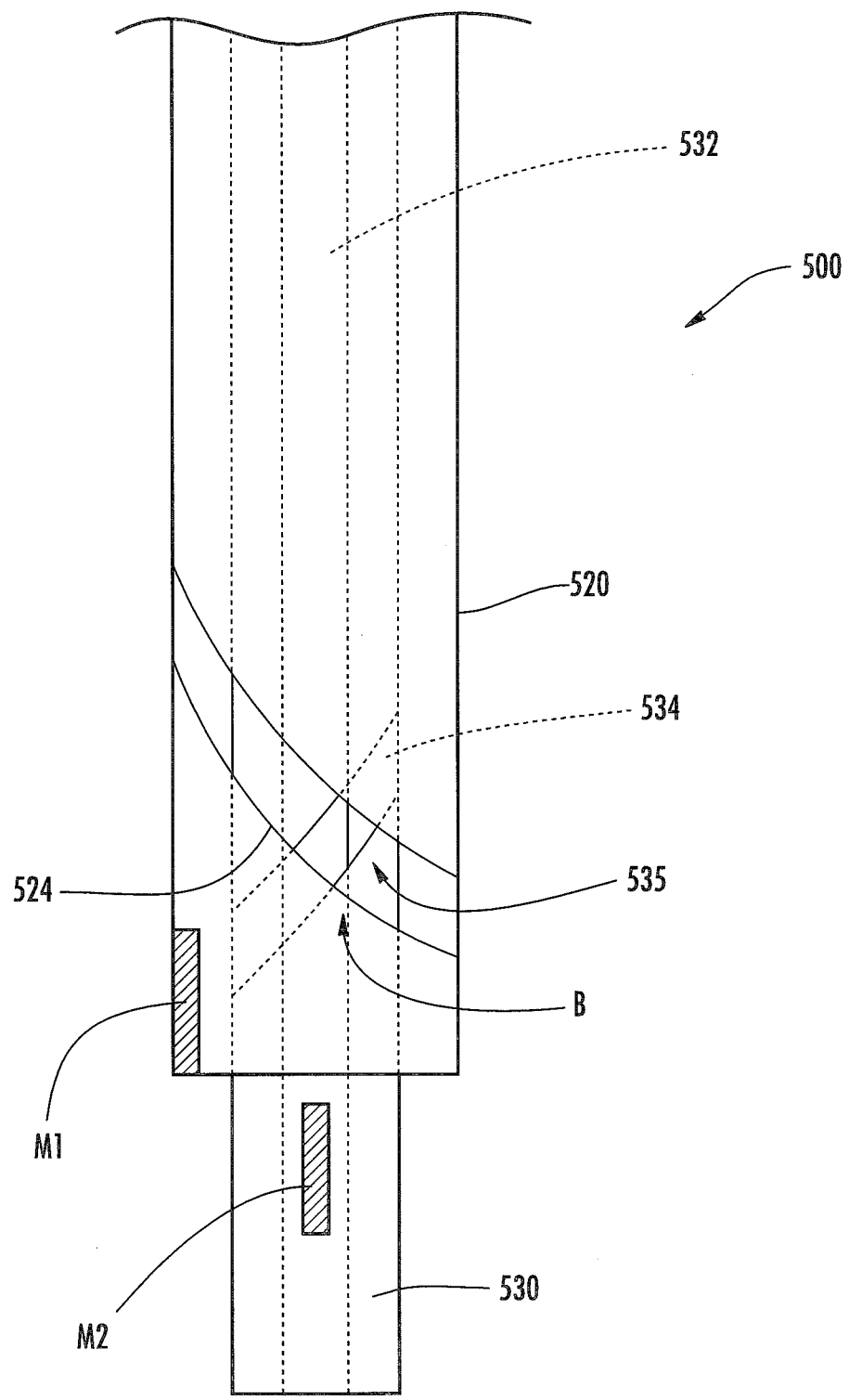
FIG. 11 is a fragmentary, side view of a surgical cannula according to further embodiments of the present invention.
Figure 12:
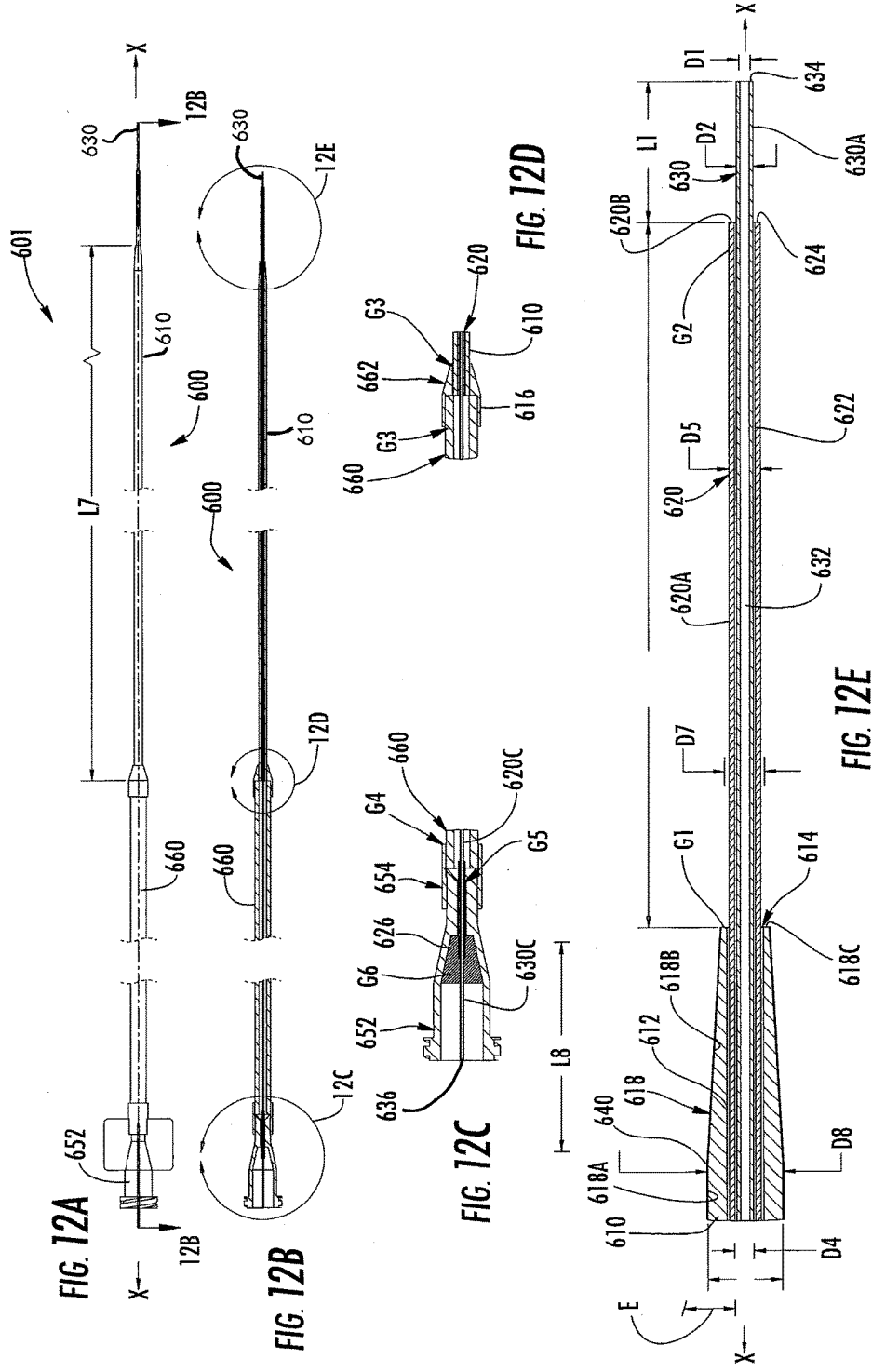
FIG. 12A is a side view of a surgical cannula according to further embodiments of the present invention.
FIG. 12B is a cross-sectional view of the surgical cannula of FIG. 12A taken along the line 12B-12B of FIG. 12A.
FIG. 12C is an enlarged, cross-sectional view of Detail 12C of FIG. 12B.
FIG. 12D is an enlarged, cross-sectional view of Detail 12D of FIG. 12B.
FIG. 12E is an enlarged, cross-sectional view of Detail 12E of FIG. 12B.

With reference to FIG. 11, an alternative MRI-compatible intrabody surgical cannula (e.g., delivery cannula) 500 according to embodiments of the present invention is shown therein and may be used in place of the cannula 100. The surgical cannula 500 includes a tubular outer sleeve 520 and a tubular inner sleeve 530 slidably mounted in the outer sleeve 520 to permit relative rotation between the sleeves 520, 530. The inner sleeve 530 defines a central lumen 532 and a helical exit slot 534. The outer sleeve 520 defines a helical exit slot 524. The area of intersection or overlap B between the exit slots 524, 534 defines an effective exit port 535. In use, the outer and inner sleeves 520, 530 can be selectively relatively rotated to change the location of the area of intersection B and thereby the axial position of the exit port 535 along the length of the surgical cannula 500.

In the case of a surgical cannula having side ports (e.g., the cannulae 300, 400, 500), the terminal end of the lumen may be closed so that there is no exit port corresponding to the exit port 116 (FIG. 5). According to some embodiments, an endwise exit port corresponding to the exit port 116 is provided, but a mechanism is provided to selectively close the endwise exit port (e.g., when a "side firing" exit port 324a, 435, 535 is opened).

In the case of surgical cannulae such as the surgical cannulae of FIGS. 9A-11 having relatively movable sleeves or other components, features may be provided to allow tracking or determine the relative positions of the components (e.g., the inner and outer sleeves). In particular, it may be desirable to enable such assessment while the delivery surgical remains in situ. Exemplary mechanisms are discussed hereinbelow with reference to FIGS. 9A, 9B and 11; however, it will be appreciated that the several different mechanisms can be used on surgical cannula of different designs than those with which they are depicted.

As discussed herein, properties of the surgical cannula may be predefined or known a priori to the circuit 30c or the operator. Such properties may include the size and geometry of the surgical cannula as well as the available cannula component settings or relationships affecting or determining functional characteristics of the surgical cannula with respect to substance flow. The available component settings or relationships may include the ranges of motion between cannula components (e.g., between the inner and out sleeves) and the alternative cannula configurations resulting from different relative positions of the components. The variable functional characteristics may include the size, number, shape, nozzle angle or direction, axial position along the cannula, and/or circumferential position of the exit port(s) of each of the inner and outer sleeves or of the effective exit ports(s).

Using this knowledge of the characteristics of the surgical cannula in combination with determination of the present positions of the pertinent cannula components with respect to one another and/or with respect to the patient anatomy, the circuit 30c or operator can make suitable modifications to the surgical cannula in situ to reconfigure the surgical cannula to new settings (and, in some cases, reposition the delivery cannula with respect to the patient anatomy) and thereby modify one or more of the aforementioned functional characteristics.

By way of example, a delivery cannula may be inserted as described herein and delivery of the substance may be begun. The operator, referring to the displayed visualization of the patient or in accordance with a prescribed protocol, may wish to subsequently revise the settings to deliver the substance from the same general location but in a different radial direction. The operator can obtain the desired new settings by adjusting or manipulating the delivery cannula in accordance with the pre-known characteristics of the delivery cannula and the current position/configuration of the delivery cannula as determined from the MR image data. Likewise, in some embodiments, the circuit 30c can programmatically evaluate the MR data to determine the current position/configuration of the delivery cannula, determine the adjustments needed to achieve a desired new cannula configuration to provide a corresponding new substance flow pattern or flow rate, and report the necessary adjustments to the operator. The adjustments may be adjustments of the components relative to one another (e.g., rotating the inner sleeve 430 relative to the outer sleeve 420 to adjust the size of the effective exit port 435) and/or relative to the patient (e.g., rotating the outer sleeve 420 relative to the target to adjust the angle or direction of flow from the effective exit port 435). Methods and apparatus as described can thus provide for improved or precise adjustment and control over the location and characteristics (e.g., direction and flow rate) of the flow of the substance dispensed from the delivery cannula.

According to some embodiments and with reference again to FIG. 11, MRI-visible marks M1, M2 or fiducial markers are mounted on the outer sleeve 520 and the inner sleeve 530, respectively. The MRI-visible mark M1 travels with the sleeve 520 and the MRI-visible mark M2 travels with the sleeve 530. The marks M1, M2 each appear in the MR image as displayed on the UI so that the operator can observe their relative rotational positions and thereby determine the location or pattern of the effective exit port 535. A look up chart or the like may be provided to assist the operator in this determination.

Alternatively, the MRI-visible marks M1, M2 may be scanned and processed by the circuit 30c. The system 10 may programmatically determine the corresponding exit port configuration and report the same to the operator via the UI. Alternatively, the operator can select a desired delivery flow rate and/or flow pattern and the system can programmatically correlate the substance to the position of the sleeves and instruct the operator as to the rotation required.

According to some embodiments and with reference again to FIG. 9B, an electronic position sensor device 72 is mounted on the surgical cannula 300. The electronic position sensor device 72 may include an encoder, for example, that generates digital pulses to the circuit 30c corresponding to the relative rotational positions of the sleeves 320, 330. The system 10 may programmatically determine the corresponding exit port configuration and report the same to the operator via the UI.

With reference to FIGS. 12A-12E, a cannula system 601 according to embodiments of the present invention is shown therein. The system 601 includes an MRI-compatible intrabody surgical (e.g., delivery) cannula 600 (hereinafter, the delivery cannula 600) particularly well-suited for delivering a substance to a patient, connecting tubing 660, and a luer fitting (e.g., luer lock) 652. The system 601 may be used in place of the cannula 100 and the connecting tubing 84.

The cannula 600 includes a rigid tubular support sleeve 610. The support sleeve 610 defines an axially extending central lumen 612. An exit opening 614 on the distal end of the support sleeve 610 and an inlet opening 616 on the proximal end of the support sleeve 610 each fluidly communicate with the lumen 612. The outer surface 618 of the support sleeve 610 includes a proximal section 618A having a substantially uniform diameter D8. The outer surface 618 also includes a distal section 618B having a tapered or frusto-conical shape that tapers in the axial distal direction. The outer surface 618 further includes distal end face 618C.

According to some embodiments, the support sleeve 610 is formed of a substantially rigid MRI-compatible material. According to some embodiments, the support sleeve 610 is formed of an MR safe material. According to some embodiments, the MRI-compatible material is a ceramic. Suitable ceramics may include Alumina. Other MRI-compatible materials that may be used for the sleeve 610 may include glass or rigid polymers.

A conformal outer polymeric sleeve 640 surrounds and fits tightly about the support sleeve 610. According to some embodiments, the polymeric sleeve 640 is formed of polyethylene terephthalate (PET). According to some limits, the polymeric sleeve 640 is an elastomeric shrinkable sleeve.

The inner sleeve 620 extends through the lumen 612. The inner sleeve 620 is secured to the inner surface of the support sleeve 610. According to some embodiments, the inner sleeve 620 is bonded to the inner surface of the support sleeve 610 by a layer of adhesive G1 such as LOCTITE® 4014 adhesive.

The inner sleeve 620 defines an axially extending central lumen 622. An exit opening 624 on the distal end of the inner sleeve 620 and an inlet opening 626 on the proximal end of the inner sleeve 620 each fluidly communicate with the lumen 622. An extension section 620A of the inner sleeve 620 extends beyond the distal end of the support sleeve 610 and is exposed. The distal end of the inner sleeve 620 defines a distal end face 620B. A proximal extension section 620C of the inner sleeve 620 extends beyond the proximal end of the support sleeve 610 and through the connecting tubing 660 to an infusion pump, for example.

According to some embodiments, the inner sleeve 620 is formed of a substantially rigid MRI-compatible material. According to some embodiments, the MRI-compatible material is fused silica.

A transfer tube 630 extends through the lumen 622. The transfer tube 630 is secured to the inner surface of the inner sleeve 620. According to some embodiments, the transfer tube 630 is bonded to the inner surface of the inner sleeve 620 by a layer of adhesive G2, such as LOCTITE® 4014 adhesive.

The transfer tube 630 defines an axially extending central lumen 632. An exit opening 634 on the distal end of the transfer tube 630 and an inlet opening 636 on the proximal end of the transfer tube 630 each fluidly communicate with the lumen 632. A distal extension section 630A of the transfer tube 630 extends beyond the distal end of the inner sleeve 620 and is exposed. A proximal extension section 630C (FIG. 12C) of the transfer tube 630 extends beyond the proximal end of the support sleeve 610 and through the connecting tubing 660 to an infusion pump, for example.

According to some embodiments, the transfer tube 630 is formed of a substantially rigid MRI-compatible material. According to some embodiments, the MRI-compatible material is fused silica.

The connecting tubing 660 (FIGS. 12B, 12C and 12D) is coupled to the proximal end of the support sleeve 610 by a tubing adapter 662. The tubing adapter 662 may be bonded to the support sleeve 610 and the connecting tubing 660 by an adhesive G3, such as LOCTITE™ UV 3311 adhesive. The connecting tubing 660 may be formed of any suitable MRI compatible material. According to some embodiments, the connecting tubing 660 is formed of polyvinyl chloride (PVC). According to some embodiments, the connecting tubing 660 is formed of silicone. The tubing adapter 662 may be formed of any suitable MRI compatible material, such as an MRI-compatible polymer.

The luer fitting 652 is coupled to the proximal end of the connecting tubing 660 by a luer adapter 654. The luer adapter 654 may be bonded to the luer fitting 652 and the connecting tubing 660 by an adhesive G4, such as LOCTITE™ UV 3311 adhesive. The luer adapter 654 may be formed of any suitable MRI compatible material, such as an MM-compatible polymer. The luer fitting 652 may also be bonded to the inner sleeve 620 by one or more the adhesives G5, G6, such as LOCTITE® UV 3311 adhesive and/or LOCTITE® UV 4014 adhesive.

According to some embodiments, the inner diameter D1 of the transfer tube 630 is in the range of from about 10 μm to 1 mm and, in some embodiments, is about 200 μm. According to some embodiments, the outer diameter D2 of the transfer tube 630 is in the range of from about 75 μm to 1.08 mm and, in some embodiments is about 360 μm. According to some embodiments, the length L1 of the exposed section 630A of the transfer tube 630 is in the range of from about 1 mm to 50 mm and, in some embodiments is about 3 mm.

According to some embodiments, the inner diameter D4 of the inner sleeve 620 is in the range of from about 85 μm to 1.1 mm and, in some embodiments, is about 450 μm. According to some embodiments, the outer diameter D5 of the inner sleeve 620 is in the range of from about 150 μm to 1.5 mm and, in some embodiments, is about 673 μm. According to some embodiments, the length L4 of the exposed section 620A of the inner sleeve 620 is in the range of from about 1 mm to 75 mm and, in some embodiments is about 15 mm.

According to some embodiments, the inner diameter D7 of the support sleeve 610 is in the range of from about 160 μm to 1.55 mm and, in some embodiments, is about 750 μm. According to some embodiments, the outer diameter D8 of the uniform diameter section 618A of the support sleeve 610 is in the range of from about 500 μm to 4 mm and, in some embodiments, is about 1.6 μm. According to some embodiments, the overall length L7 of the support sleeve 610 is in the range of from about 0.5 inch to 20 inches and, in some embodiments, is in the range of from about 10 to 14 inches. According to some embodiments, the length L8 of the tapered section 618B of the support sleeve 610 is in the range of from about 6 to 9 mm.

According to some embodiments, the thickness of the conformal polymeric sleeve 640 is in the range of from about 40 to 60 μm. According to some embodiments, the length of the conformal polymeric sleeve 640 is substantially coextensive with the support sleeve 610.

As best seen in FIG. 12E, the cannula 600 is a stepped cannula with three co-axially disposed step segments (the outer surfaces of the transfer tube 630, the inner sleeve 620 and the conformal polymeric sleeve 640, respectively) having different outer diameters and separated by the steps or rises of the end faces 618C, 620B.

The cannula 600 may be a unitary, integral structure having no relatively slidably elements.

The cannula 600 may be used in the same manner as described herein with respect to the cannula 100, for example. The luer can be operatively coupled to an infusion pump (e.g., the infusion pump 82) or syringe, which supplies a mass flow of the desired substance or material to be delivered into the patient.

The cannula 600 can provide a number of advantages. The rigid support sleeve 610 prevents or inhibits bending or flex of the large majority of the length of the cannula 600 as the cannula 600 is inserted through the targeting cannula 60 and into the patient (e.g., the brain). By restricting the axial movement of the cannula 600 during insertion, the cannula 600 can reduce or prevent small movements that may disrupt tissue and thereby lead to reflux of the infused substance. A ceramic support sleeve 610, in particular, can provide good rigidity while also being MRI-compatible and MRI safe. According to some embodiments, the entirety of the cannula 600 is formed of an MRI-compatible, MR safe material or materials.

The conformal polymeric sleeve 640 may beneficially provide a lubricious surface over the support sleeve 610 to reduce shear force on the brain or other tissue during insertion. The conformal polymeric sleeve 640 can enhance the safety of the cannula 600 by capturing the support sleeve 610 or pieces thereof if the support sleeve is accidentally broken in situ.

The steps S1, S2 and the end faces 618C, 620B can serve to reduce or prevent reflux of the delivered substance. The provision of an exposed transfer tube section 630A having the aforedescribed length L1 and inner diameter D1 has also been found to provide beneficial reflux resistance performance.

The tapered transition 618B between the outer diameter D5 of the inner sleeve 620 and the outer diameter D8 of the support sleeve 610 can provide the reflux control of the small diameter inner sleeve 620 along with a support sleeve 610 having a geometry providing satisfactory rigidity and size for cooperation with the targeting cannula 60 or adapter 74.

The protective connecting tubing 660 can serve to protect the transfer tube 630 while also permitting convenient routing the connecting tubing 660 to the infusion pump. According to some embodiments, the length L11 of the tubing 660 is in the range of from about 6 to 12 feet.

According to some embodiments, the infusate is delivered to a patient's brain through the exit opening 634 at an infusion rate in the range of from about 1 to 3 μL/minute.

As discussed herein, insertion of the surgical cannula 100 (or any other surgical, e.g., delivery, cannula) can be tracked in near real time by reference to a void in the patient tissue caused by the cannula 100 and reflected in the MR image. In some embodiments, one or more MRI-visible fiducial markers may be provided on the surgical cannula 100, MR scanned and processed, and displayed on the UI. In some embodiments, the surgical cannula 100 may itself be formed of an MRI-visible material, MR scanned and processed, and displayed on the UI.

According to some embodiments, the surgical cannula may include an embedded intrabody MRI antenna that is configured to pick-up MRI signals in local tissue during an MRI procedure. The MRI antenna can be configured to reside on a distal end portion of the surgical cannula. In some embodiments, the antenna has a focal length or signal-receiving length of between about 1-5 cm, and typically is configured to have a viewing length to receive MRI signals from local tissue of between about 1-2.5 cm. The MRI antenna can be formed as comprising a coaxial and/or triaxial antenna. However, other antenna configurations can be used, such as, for example, a whip antenna, a coil antenna, a loopless antenna, and/or a looped antenna. See, e.g., U.S. Pat. Nos. 5,699,801; 5,928,145; 6,263,229; 6,606,513; 6,628,980; 6,284,971; 6,675,033; and 6,701,176, the contents of which are hereby incorporated by reference as if recited in full herein. See also U.S. Patent Application Publication Nos. 2003/0050557; 2004/0046557; and 2003/0028095, the contents of which are also hereby incorporated by reference as if recited in full herein.

Figure 13:
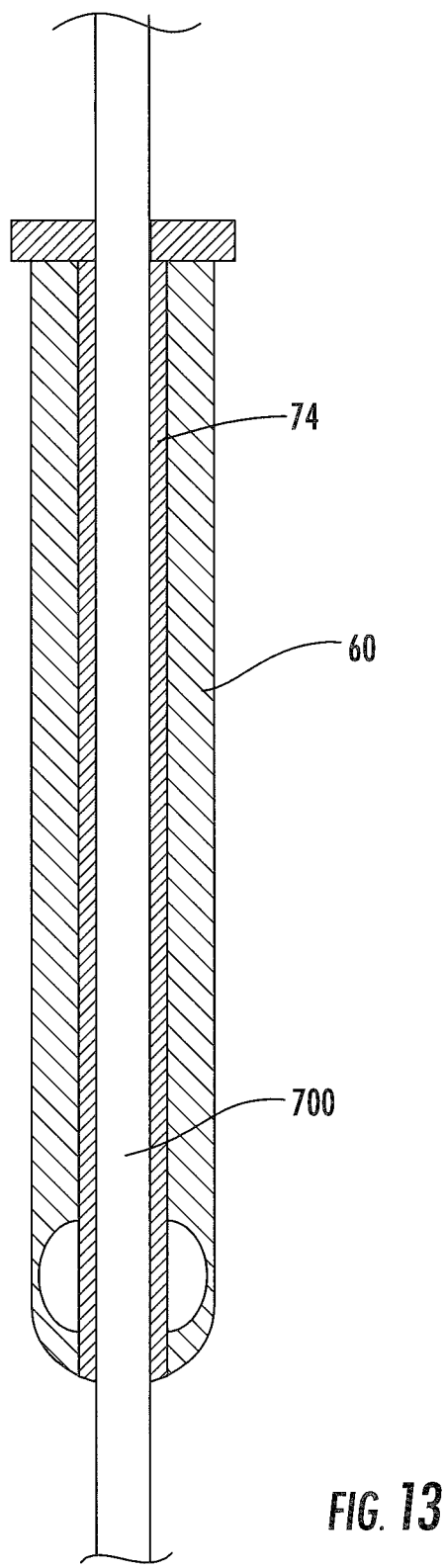
FIG. 13 is a cross-sectional view of a targeting cannula with a surgical cannula and an adapter.

According to some embodiments and with reference to FIG. 13, an adapter sleeve 74 is provided to take up the radial gap between the inner diameter of the targeting cannula 60 and the outer diameter of an MRI-compatible surgical cannula 700.

Surgical cannulae 100-700 as described herein may be used with a stereotactic frame or without a stereotactic frame.

While the surgical cannulae 100-700 have been identified herein as delivery cannulae and methods for delivering a substance to a patient have been described, in accordance with some embodiments of the invention, the surgical cannulae and methods can be used to withdraw a substance (e.g., spinal fluid) from a patient. Thus, it will be appreciated that surgical cannulae and methods as disclosed herein can be used to transfer a substance into and/or from a patient.

While the surgical cannulae 100-700 have been described herein with reference to MRI-guided insertion and infusion procedures, in some embodiments the cannulae can be used in procedures without MRI guidance.

While the surgical cannulae 100-700 have been described in use with a trajectory guide 50b, the cannulae may be used with other types of trajectory guidance or stereotactic frames or without a stereotactic frame or trajectory guide.

Figure 14A:
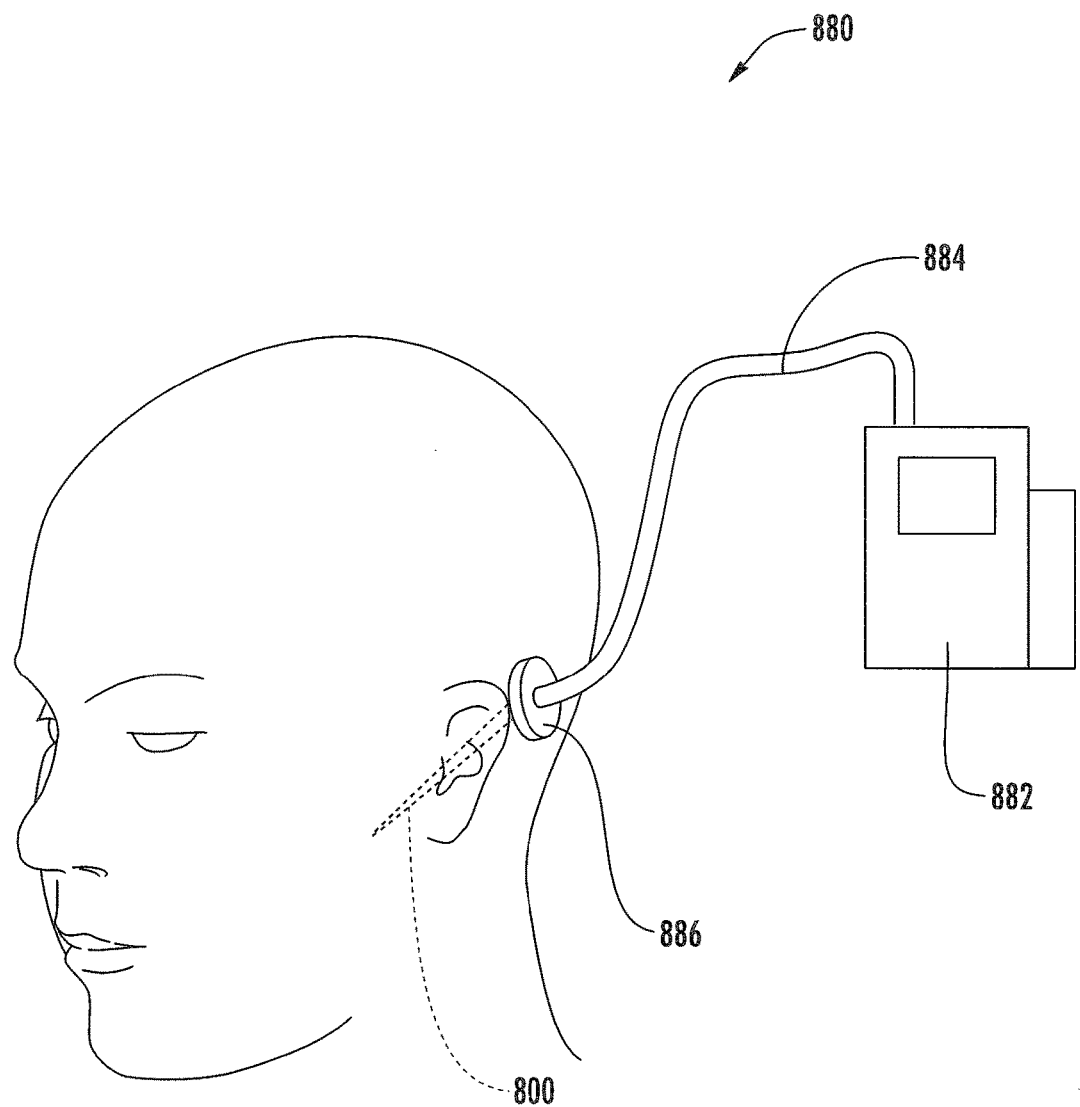
FIG. 14A is a schematic illustration of a chronic substance delivery system according to some embodiments of the present invention.
Figure 14B:
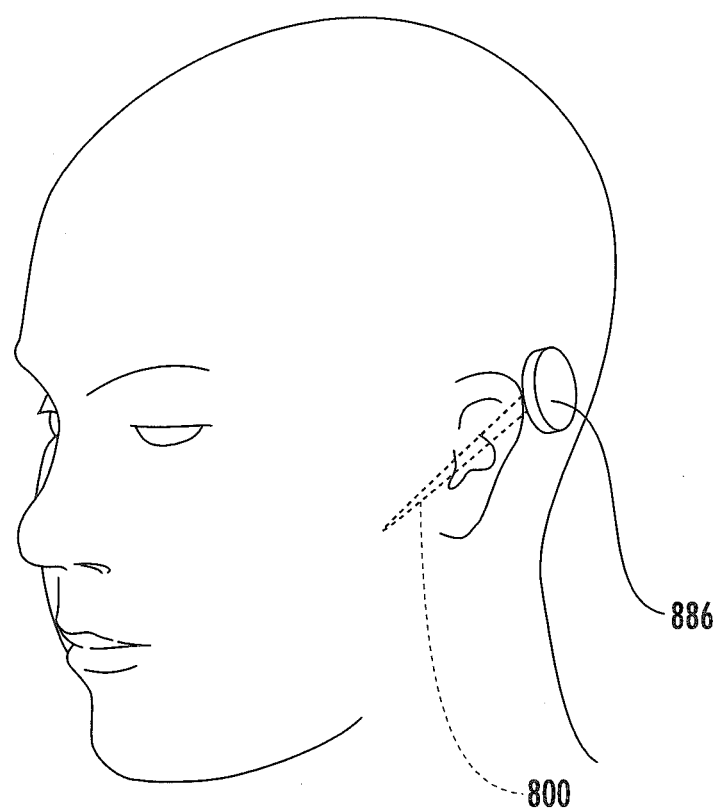
FIG. 14B is a schematic illustration of a portion of the chronic substance delivery system of FIG. 14A with an access port thereof being closed.

The surgical cannulae 100-700 as depicted in FIGS. 1-13 would typically be employed for acute treatments. However, the systems, cannulae, methods and procedures described herein may likewise be used for installation of a chronic delivery cannula or catheter. An exemplary chronic substance delivery system 880 is shown in FIG. 14. The system 880 includes a delivery cannula 800, a port device 886, connection tubing 884 and an infusion pump 882. The system 880 may be installed in the same manner as the system 80 (FIG. 1) except that the delivery cannula 800 is configured to remain in the patient post-first delivery and the port device 886 is installed on the patient (e.g., behind the patient's ear) to provide an (external) access point for subsequently releasably coupling the connection tubing 884 to the delivery cannula 800. The pump 882 can be periodically or continuously connected to the delivery cannula 800 to deliver a therapeutic substance to a target region of the patient through the delivery cannula 800. In some embodiments, the connecting tubing, the pump and substance reservoir may be implanted in the patient and connected to the delivery cannula 800 by the tubing so that the port device 886 is not needed, similar to an IPG and electrical stimulation lead. The chronic system can allow delivery of the substance or substances at different delivery times without requiring another surgical implantation procedure to place the delivery cannula. FIG. 14B illustrates the delivery cannula 800 and the port device 886 with the connection tubing 884 and the pump 882 disconnected and the port device 886 closed to cap the access path to the delivery cannula 800.

According to some embodiments, the substance delivered via the delivery cannula includes radioactive objects such as radioactive seeds. In this event, the delivery cannula may include a suitable radiation shield or shielding material in order to reduce or prevent the exposure of tissue outside the target region to radiation from the radioactive objects.

The system 10 may also include a decoupling/tuning circuit that allows the system to cooperate with an MRI scanner 20 and filters and the like. See, e.g., U.S. Pat. Nos. 6,701,176; 6,904,307 and U.S. Patent Application Publication No. 2003/0050557, the contents of which are hereby incorporated by reference as if recited in full herein.

Figure 15:
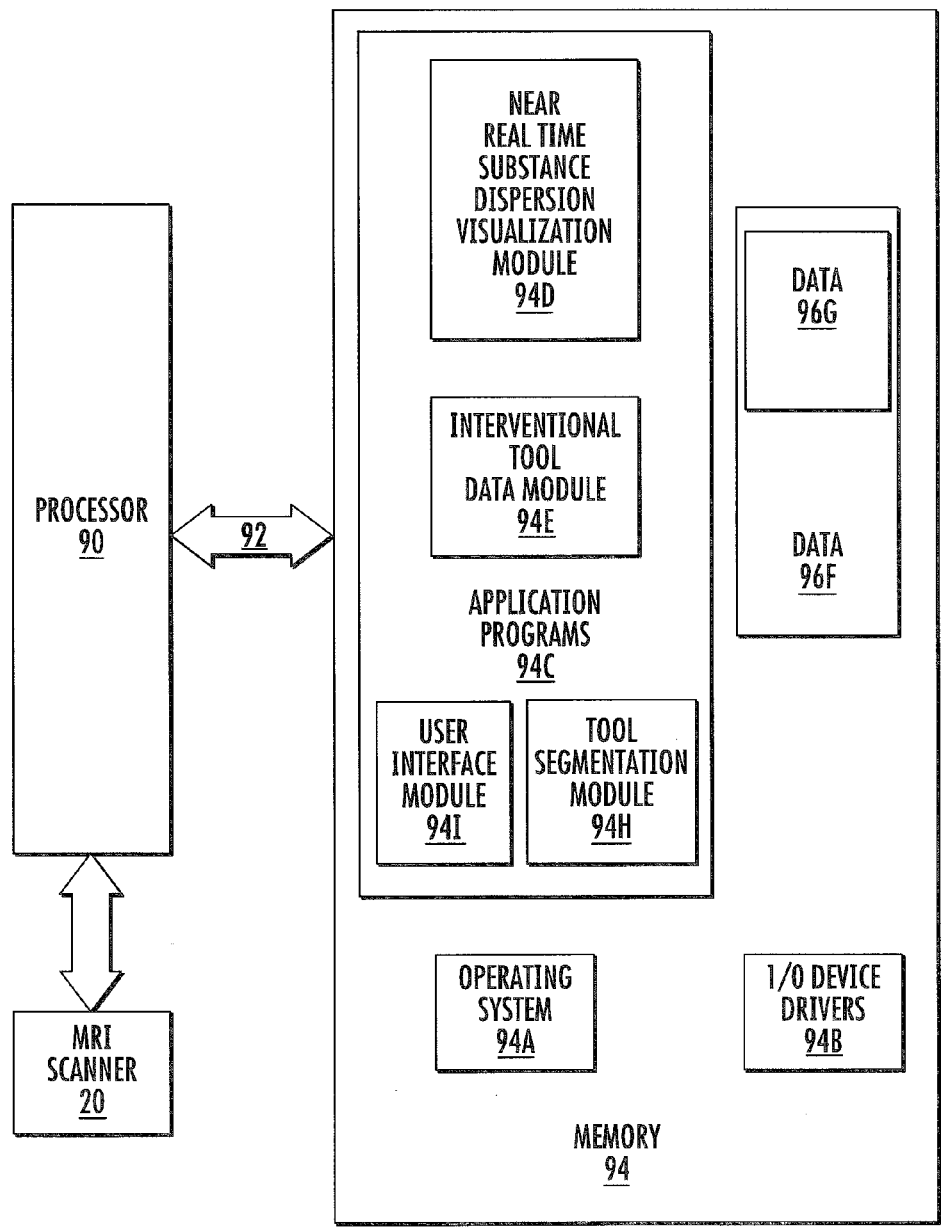
FIG. 15 is a data processing system according to some embodiments of the present invention.

The system 10 can include circuits and/modules that can comprise computer program code used to automatically or semi-automatically carry out operations to generate visualizations and provide output to a user to facilitate MRI-guided diagnostic and therapy procedures. FIG. 15 is a schematic illustration of a circuit or data processing system that can be used with the system 10. The circuits and/or data processing systems may be incorporated in one or more digital signal processors in any suitable device or devices. The processor 90 communicates with an MRI scanner 20 and with memory 94 via an address/data bus 92. The processor 90 can be any commercially available or custom microprocessor. The memory 94 is representative of the overall hierarchy of memory devices containing the software and data used to implement the functionality of the data processing system. The memory 94 can include, but is not limited to, the following types of devices: cache, ROM, PROM, EPROM, EEPROM, flash memory, SRAM, and DRAM.

The memory 94 may include several categories of software and data used in the data processing system: the operating system 94A; the application programs 94C; the input/output (I/O) device drivers 94B; and data 94F. The data 94F can also include predefined characteristics of different surgical tools and patient image data 94G. The application programs 94C can include a Near Real-Time Substance Dispersion Visualization Module 94D, Interventional Tool Data Module 94E, a Tool Segmentation Module 94H (such as segmentation modules for a targeting cannula, a trajectory guide frame and/or base, and a delivery cannula), and a workflow group User Interface Module 94I (that facilitates user actions and provides guidance to obtain a desired trajectory or a desired drug dispersion pattern, such as physical adjustments to achieve same).

As will be appreciated by those of skill in the art, the operating systems 94A may be any operating system suitable for use with a data processing system, such as OS/2, AIX, DOS, OS/390 or System390 from International Business Machines Corporation, Armonk, N.Y., Windows CE, Windows NT, Windows95, Windows98, Windows2000 or other Windows versions from Microsoft Corporation, Redmond, Wash., Unix or Linux or FreeBSD, Palm OS from Palm, Inc., Mac OS from Apple Computer, LabView, or proprietary operating systems. The I/O device drivers 94C typically include software routines accessed through the operating system 94A by the application programs 94C to communicate with devices such as I/O data port(s), data storage 94F and certain memory 94 components. The application programs 94C are illustrative of the programs that implement the various features of the data processing system and can include at least one application, which supports operations according to embodiments of the present invention. Finally, the data 94F represents the static and dynamic data used by the application programs 94C, the operating system 94A, the I/O device drivers 94C, and other software programs that may reside in the memory 94.

While the present invention is illustrated, for example, with reference to the Modules 94C, 94D, 94E, 94H, 94I being application programs in FIG. 15, as will be appreciated by those of skill in the art, other configurations may also be utilized while still benefiting from the teachings of the present invention. For example, the Modules 94C, 94D, 94E, 94H, 94I and/or may also be incorporated into the operating system 94A, the I/O device drivers 94B or other such logical division of the data processing system. Thus, the present invention should not be construed as limited to the configuration of FIG. 15, which is intended to encompass any configuration capable of carrying out the operations described herein. Further, one or more of modules, i.e., Modules 94C, 94D, 94E, 94H, 94I can communicate with or be incorporated totally or partially in other components, such as a workstation, an MRI scanner, an interface device. Typically, the workstation 30 will include the modules 94C, 94D, 94E, 94H, 94I and the MR scanner with include a module that communicates with the workstation 30 and can push image data thereto.

The I/O data port can be used to transfer information between the data processing system, the circuit 30c or workstation 30, the MRI scanner 20, and another computer system or a network (e.g., the Internet) or to other devices controlled by or in communication with the processor. These components may be conventional components such as those used in many conventional data processing systems, which may be configured in accordance with the present invention to operate as described herein.

It is noted that any one or more aspects or features described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

Figure 16:
FIG. 16 is an exemplary screen shot of a display of a User Interface during an MRI-guided infusion procedure.

FIG. 16 is an exemplary screen shot of a display of a user interface from an actual MRI-guided infusion procedure on a (monkey) brain using an intrabody cannula generally corresponding to the cannula 600. The screen shot includes an image (i.e., the white portions at the top of the screen) of the targeting cannula 60, and an image (i.e., the white portion in the brain region) of the infused substance in the brain.

Figure 17A:
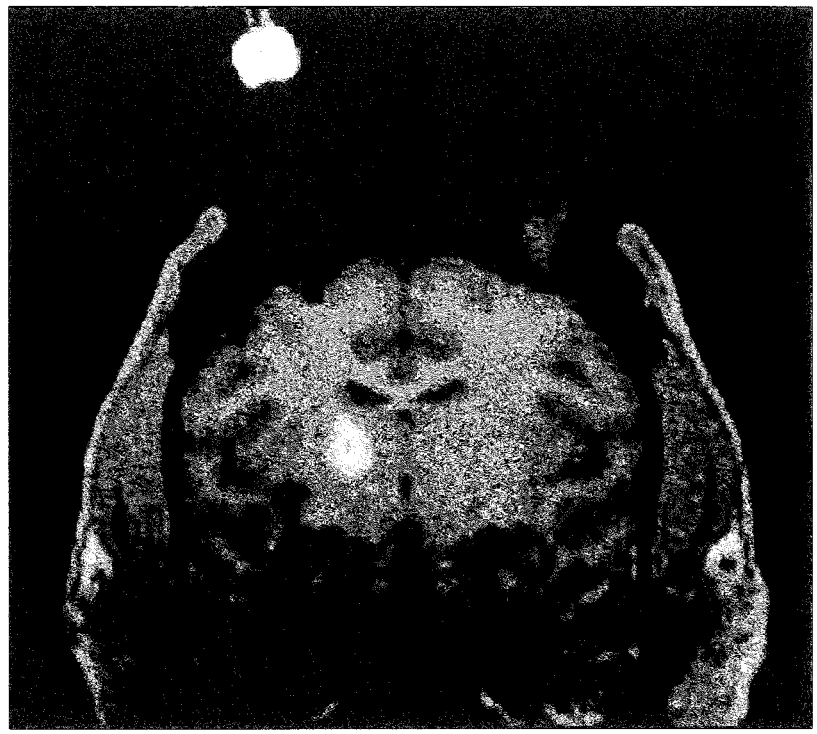
FIGS. 17A and 17B are exemplary screen shots of a display of a User Interface during an MRI-guided infusion procedure and captured at a first time and a second, subsequent time, respectively.
Figure 17B:
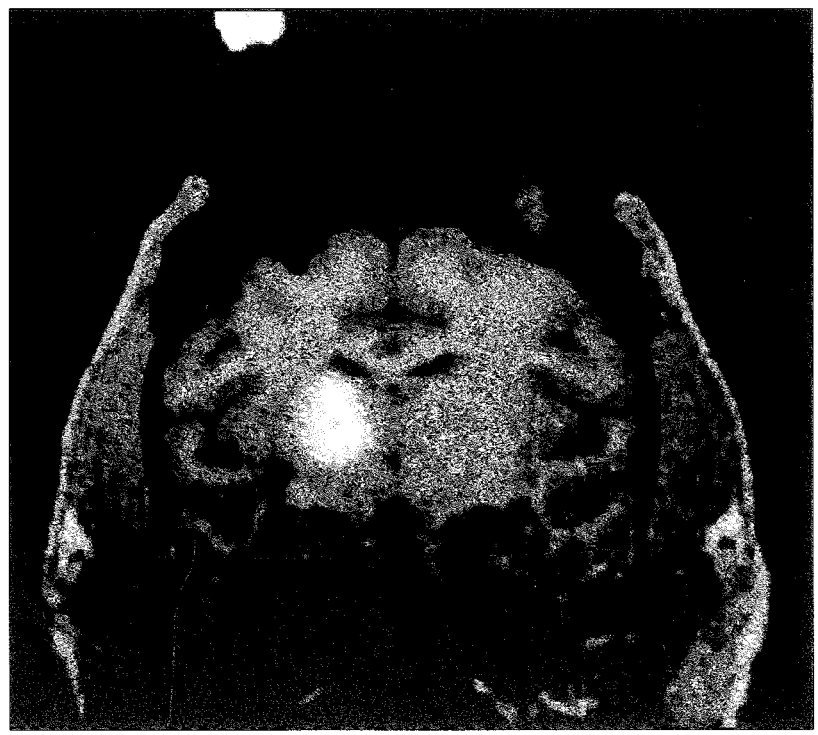

FIGS. 17A and 17B are further exemplary screen shots of a display of a user interface from an actual MRI-guided infusion procedure on a (monkey) brain using an intrabody cannula generally corresponding to the cannula 600. The screen shots of FIGS. 17A and 17B each include an image (i.e., the white portions at the top of the screen) of the targeting cannula as well as images (i.e., the white portion in the brain region) of the substance infused into the brain. The screen shot of FIG. 17A was captured at a first time in the procedure and the screen shot of FIG. 17B was captured at a second subsequent time during the procedure. The distribution and dispersion pattern of the infused substance in the brain, as well as the change in the distribution and dispersion pattern of the infused substance in the brain, can be readily appreciated and tracked by reference to the screen shots of FIGS. 17A and 17B.

Other systems, methods, and/or computer program products according to embodiments of the invention will be or become apparent to one with skill in the art upon review of the following drawings and detailed description. It is intended that all such additional systems, methods, and/or computer program products be included within this description, be within the scope of the present invention, and be protected by the accompanying claims.

In the drawings and specification, there have been disclosed embodiments of the invention and, although specific terms are employed, they are used in a generic and descriptive sense only and not for purposes of limitation, the scope of the invention being set forth in the following claims. Thus, the foregoing is illustrative of the present invention and is not to be construed as limiting thereof. More particularly, the workflow steps may be carried out in a different manner, in a different order and/or with other workflow steps or may omit some or replace some workflow steps with other steps. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A cannula for transferring a substance to and/or from a patient, the cannula comprising:
    a rigid tubular support sleeve defining a lumen extending from an inlet opening at a proximal end of the tubular support sleeve to an exit opening at a distal end of the tubular support sleeve;
    a transfer tube positioned in the lumen and extending fully through the inlet opening, the lumen and the exit opening, the transfer tube including a proximal extension section extending beyond the proximal end of the tubular support sleeve and a distal extension section extending beyond the distal end of the tubular support sleeve; and
    an inner sleeve disposed in the tubular support sleeve and extending beyond the distal end of the tubular support sleeve, wherein the transfer tube has a length that is greater than that of the tubular support sleeve, the transfer tube extends fully through the inner sleeve, the proximal extension section extends beyond a proximal end of the inner sleeve, and the distal extension section extends beyond a distal end of the inner sleeve;
    wherein the tubular support sleeve comprises a rigid, MRI-compatible material;
    wherein the transfer tube is adhered with adhesive to an inner surface of the inner sleeve; and
    wherein:
        the transfer tube has an exit opening at a distal end of the distal extension section of the transfer tube and from which the substance is dispensed in use;
        an exterior surface of the cannula has at least first, second and third co-axially disposed segments, an outer diameter of the second segment being greater than an outer diameter of the first segment and an outer diameter of the third segment being greater than the outer diameter of the second segment;
        the first segment extends from the distal end of the distal extension section of the transfer tube;
        the second segment extends between and adjoins each of the first and third segments;
        the second segment includes a first end face defining a first step between the first segment and the second segment, the first end face projecting radially outwardly beyond the outer diameter of the first segment;
        the third segment includes a second end face defining a second step between the second segment and the third segment, the second end face projecting radially outwardly beyond the outer diameter of the second segment; and
        the third segment is longer than each of the first and second segments.

2. The cannula of claim 1 wherein the tubular support sleeve comprises a ceramic material.

3. The cannula of claim 2 including a conformal polymeric sleeve surrounding the tubular support sleeve.

4. The cannula of claim 3 wherein the conformal polymeric sleeve is an elastomeric shrink tubing.

5. The cannula of claim 1 including a conformal polymeric sleeve surrounding the tubular support sleeve.

6. The cannula of claim 5 wherein the conformal polymeric sleeve is an elastomeric shrink tubing.

7. The cannula of claim 5 wherein the conformal polymeric sleeve extends substantially coextensive with the tubular support sleeve from the proximal end of the tubular support sleeve to the distal end of the tubular support sleeve.

8. The cannula of claim 1 wherein the exterior surface includes a tapered transition between the third and second segments.

9. The cannula of claim 1 wherein the transfer tube is formed of fused silica.

10. The cannula of claim 1 wherein the tubular support sleeve has a length of at least 10 inches.

11. The cannula of claim 1 wherein an outer surface of the tubular support sleeve has a size and geometry adapted for use with a stereotactic frame.

12. The cannula of claim 1 including a silicone or polyvinyl chloride (PVC) protective tubing extending from the proximal end of the tubular support sleeve, wherein the proximal extension section of the transfer tube extends through the protective tubing.

13. The cannula of claim 12 wherein the protective tubing is bonded to the proximal end of the tubular support sleeve.

14. The cannula of claim 1 wherein the transfer tube is a continuous unitary tube formed of fused silica.

15. The cannula of claim 1 wherein:
    the first end face is the distal end of the inner sleeve;
    the second end face is the distal end of the tubular support sleeve;
    the first segment extends from the distal end of the distal extension section of the transfer tube to the distal end of the inner sleeve;
    the second segment extends from the distal end of the inner sleeve to the distal end of the tubular support sleeve; and
    the tubular support sleeve includes a tapered transition from the distal end of the tubular support sleeve to an outer diameter of the tubular support sleeve.

16. The cannula of claim 1 wherein the inner sleeve is formed of a substantially rigid material.

17. The cannula of claim 16 wherein the inner sleeve is adhered with adhesive to an inner surface of the tubular support sleeve.

18. The cannula of claim 17 wherein:
the cannula includes a conformal polymeric sleeve surrounding the tubular support sleeve;
the conformal polymeric sleeve extends substantially coextensive with the tubular support sleeve from the proximal end of the tubular support sleeve to the distal end of the tubular support sleeve; and
the tubular support sleeve comprises a ceramic material.

19. The cannula of claim 1 wherein the inner sleeve is adhered with adhesive to an inner surface of the tubular support sleeve to thereby increase a stiffness of the cannula.

* * * * *